United States Patent
Hone et al.

(10) Patent No.: US 6,759,241 B1
(45) Date of Patent: Jul. 6, 2004

(54) ADJUVANT COMPRISING A LIPOPOLYSACCHARIDE ANTAGONIST

(75) Inventors: David M. Hone, Ellicott City, MD (US); Richard Crowley, Solana Beach, CA (US); Mohamed Tarek Shata, New York, NY (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 38 days.

(21) Appl. No.: 10/110,072

(22) PCT Filed: Oct. 4, 2000

(86) PCT No.: PCT/US00/27402

§ 371 (c)(1),
(2), (4) Date: Feb. 27, 2003

(87) PCT Pub. No.: WO01/25254

PCT Pub. Date: Apr. 12, 2001

Related U.S. Application Data

(60) Provisional application No. 60/192,650, filed on Mar. 27, 2000, and provisional application No. 60/157,635, filed on Oct. 4, 1999.

(51) Int. Cl.[7] .............................. C12N 5/02; C12N 1/00; G01N 33/53; A61K 39/38; A61K 39/07
(52) U.S. Cl. ....................... 435/325; 435/7.2; 435/810; 424/184.1; 424/234.1
(58) Field of Search ................................ 435/810, 325; 435/7.2; 424/184.1, 234.1

(56) References Cited

U.S. PATENT DOCUMENTS

| | | |
|---|---|---|
| 5,091,513 A | 2/1992 | Huston et al. |
| 5,158,939 A | 10/1992 | Takayama et al. |
| 5,189,674 A | 2/1993 | Shimizu |
| 5,191,072 A | 3/1993 | Hasegawa et al. |
| 5,288,637 A | 2/1994 | Roth |
| 5,593,969 A | 1/1997 | Kamireddy et al. |
| 5,827,816 A | 10/1998 | Theofan et al. |
| 5,837,810 A | 11/1998 | Han et al. |
| 5,856,438 A | 1/1999 | Little, II |
| 5,869,055 A | 2/1999 | Juan et al. |
| 5,877,159 A | 3/1999 | Powell et al. |

FOREIGN PATENT DOCUMENTS

| | | |
|---|---|---|
| WO | WO 93/13198 | 7/1993 |
| WO | WO 99/15162 | 4/1999 |

OTHER PUBLICATIONS

PCT References were considered.*
Al–Hendy, et al., "Lipopolysaccharide O side chain *Yersinia enterocolitica* o:3 is an essential virulence factor in an orally infected murine model." 1992, Infect. Immun., 60:870–875.
Alegre, et al., "Immunomodulation of transplant rejection using monoclonal antibodies and soluble receptors." 1995, Digest Dis. Sci., 49:58–64.
Alving, "Liposomes as carriers of antigens and adjuvants." 1991, J. Immunol. Meth., 140:1–13.
Alving and Richards, "Liposomes containing lipid A: a potent nontoxic adjuvant for a human malaria sporozoite vaccine." 1990, Immunol. Lett., 25:275–280.
Banerji, et al., "Expression of a b–globin gene is enhanced by remote SV40 DNA sequences." 1981, Cell, 27:299–308.
Bashir, et al. Evaluation of defined antigen vaccines against *Schistosoma bovis* and *S. japonicum* in bovines, 1994, Trop. Geog., 46:255–258.

(List continued on next page.)

*Primary Examiner*—Hankyel T. Park
(74) *Attorney, Agent, or Firm*—Marianne Fuierer; Steven J. Hultquist; Yongzhi Yang

(57) ABSTRACT

LPS preparations, isolated from gram negative bacterial strains that contain at least one mutation in at least one of the htrB and msbB genes, and methods and therapeutics related thereto. The LPS preparations display both LPS antagonist and adjuvant activities.

55 Claims, 3 Drawing Sheets

OTHER PUBLICATIONS

Berglund, et al., "Immunization with recombinant Semliki Forest virus induces protection against influenza challenge in mice." 1999, Vaccine, 17:497–507.

Chamberlain, et al., "*Neisseria gonorhorea* strain MS11 harbouring a mutation in gene aroA is attenuated and immunogenic." 1993, Micro. Path., 15:51–63.

Chatfield, et al., "Construction of a genetically defined *Salmonella typhi* Ty2 aroA, aroC mutant for the engineering of a candidate oral typhoid—tetanus vaccine." 1992, Vaccine 10:53–60.

Chiodini and Davis, "The cellular immunology of bovine paratuberculosis: the predominant response is mediated by cytotoxic gamma/delta T lymphocytes which prevent CD4 activity." 1992, Microbial. Pathogenesis, 13;447–463.

Christ, et al., "Total synthesis of the proposed structure of *Rhodobacteria sphaeroides* lipid A resulting in the synthesis of new potent lipopolysaccharide antagonists." 1994, Am. Chem. Soc., 116:3637–3638.

Clementz, et al., "Function of the htrB high temperature requirement gene of *Escherichia coli* in the Acylation of lipid A." 1996, J. Biol. Chem., 271:12095–12102.

Clementz, et al., "Function of the *Escherichia coli* msbB gene, a multicopy suppression of htrB knockouts, in the acylation of lipid A." 1997, J. Biol. Chem., 272:10353–10360.

Colotta, et al., "Expression of a monocyte chemotactic cytokine by human mononuclear phagocytes." 1992, J. Immunol., 148:760–765.

Coulie, et al., "Genes coding for tumor antigens recognized by human cytolytic T lymphocytes." 1993, J . Immunother., 14:104–109.

Davis, et al., "CpG DNA is a potent enhancer of specific immunity in mice immunized with recombinant hepatitis B surface antigen." 1998, J. Immunol., 160:870–876.

Donnenberg, et al., "Internalization of *Escherichia coli* into human kidney epithelial cells: comparison of fecal and pyelonephritis–associated strains." 1994, J. Infect. Dis., 169:831–8.

Duke et al. "Sequence and structural elements that contribute to efficient encephalomyocarditis virus RNA translation." Jour. Of Vir. 1992: 1602–1609.

Edelman, "Vaccine Adjuvants." 1980, Rev. Infect. Dis., 2:370–383.

Eggesbo, et al., "LPS–induced release of IL–1B, IL–6, IL–8, TNF–a and sCD14 in whole blood and PBMC from persons with high or low levels of HDL–lipoprotein." 1994, Cytokine, 6:521–529.

Eldridge, et al., "New advances in vaccine delivery systems." 1993, Semin. Hematol., 30:16–25.

Eldridge, et al., "Biodegradable and biocompatible poly) DL–lactide–Co–Glycolide) micospheres as an adjuvant for staphylococcal enterotoxin B toxoid which enhances the level of toxin–neutralizing antibodies." 1991, Infect. Immun., 59:2978–2986.

Fagan, et al., 1994, "Acyclic analogue of lipid A stimulates TNF–a and arachidonate release via a unique LPS–signaling pathway." J. Immunol., 153:5230–5238.

Fairweather, et al., "Oral vaccination of mice against tetanus by use of a live attenuated salmonella carrier." 1990, Infect. Immun., 58:1323–26.

Ferrero et al., "CD14 is a member of the family of leucine–rich proteins and is encoded by a gene syntenic with multiple receptor genes." 1990, J. Immunol., 145:331–336.

Fischl, et al., "The efficacy of azidothymidine (AZT) in the treatment of patients with AIDS and AIDS–related complex." 1987, N. Engl. J. Med. 317:185–191.

Formal, et al., "Construction of a potential bivalent vaccine strain." 1981, Infect. Immun., 34:746–50.

Forrest, et al., "Immunogenicity of a candidate live oral typhoid/cholera hybrid vaccine in humans." 1989, J. Infect. Dis., 159:145–46.

Frenkel, et al., "The isolation, characterization and cloning of a globin–like, host–protective antigen from the excretory–secretory products of *Trichostrongylus colubriformis*." 1992, Mol. Biochem. Parasitol., 50:27–36.

Fromm and Berg, "Deletion mapping of DNA regions required for SV40 early region promoter function in vivo." 1982, J. Mol. Appl. Genetics, 1:457–481.

Galanos, et al., "A new method for the extraction of R lipopolysaccharides." 1969, Eur. J. Biochem., 9:245–249.

Galanos, et al., "Endotoxic properties of chemically synthesized lipid A part structures." 1984, Eur. J. Biochem., 140:221–227.

Garett, et al., "Identification of the gene encoding the *Escherichia coli* Lipid A 4'–kinase." 1997, J. Biol. Chem., 272:21855–21864.

Garret, et al., "Accumulation of a lipid a precursor lacking the 4'–phosphate following inactivation of the *Escherichia coli* lpxK gene." 1998, J. Bio. Chem., 273:12457–12465.

Gattuso, et al., "Adenosquamous carcinoma of the prostate." 1995, Human Pathol., 26:123–126.

Goldblatt, "Recent developments in bacterial conjugate vaccines." 1998, Med. Microbiol., 47:563–567.

Golenbock, et al., "Elimination and tissue distribution of the monosaccharide lipid A precursor, lipid X, in mice and sheep." 1988, Antimicrob. Agents Chemother., 32:37–41.

Golenbock, et al., "Lipid A–like molecules that antagonize the effects of endotoxins on human monocytes." 1991, J. Biol. Chem., 266:19490–19498.

Gorfinkiel, et al., "Sequence and regulation of the uapA gene encoding a uric acid–xanthine permease in the fungus *Aspergillus nidulans*." 1993, J. Biol. Chem., 268:23376–23381.

Grant, et al., "Differential plasmid rescue from transgenic mouse DNA into *Escherichia coli* methylation–restriction mutants." 1990, Proc. Natl. Acad. Sci. USA., 87:4645–4649.

Gray et al., "Cloning of the cDNA of a human neutrophil bactericidal protein." 1989, J. Biol. Chem., 264:9505–9509.

Green, et al., "Prediction of human rotavirus serotypes by nucleotide sequence analysis of the VP7 protein gene." 1988, J. Virol., 62:1819–1823.

Guadagni, et al., "In vitro and in vivo regulation of human tumor antigen expression by human recombinant interferons: a review." 1994, Int. J. Biol. Markers, 9:53–60.

Guiso, et al., "Protective activity of Bordetella adenylate cyclase–hemolysin against bactericidal colonization." 1991, Micro. Path., 11:423–31.

Hagen, et al., "Analysis of a monophosphoryl lipid A immunostimulant preparation from *Salmonella minnesota* R595 by high–performance liquid chromatography." 1997, J. Chromatogr., 767:53–61.

Hamann, et al., "Components of gut bacteria as immunomodulators." 1998, Int. J. Food Microbiol., 41:141–154.

Harborne, et al., "Transcriptional control, translation and function of the products of the five open reading frames of the *Escherichia coli* nir operon." 1992, Mol. Micro., 6:2805–2813.

Hillyer, et al., "*Fasciola hepatica:* Host responders and nonresponders to parasite glutathione S–transferase." 1992, Exp. Parasitol., 75:176–186.

Ho, et al., "Rapid turnover of plasma virions and CD4 lymphocytes in HIV–1 infection." 1995, Nature, 373:123–126.

Hogan and Vogel, "Lipid A–associated proteins provide an alternate "second signal" in the activation of recombinant interferon–y–primed, C3H/HeJ macrophages to a fully tumoricidal state." 1987, J. Immunol., 139:3697–3702.

Hogan and Vogel, "Production of tumor necrosis factor by rIFN–y–primed C3H/HeJ (Lpsd$^d$) macrophages requires of the presence of lipid A–associated proteins." 1988, J. Immunol., 141:4196–4202.

Homma, et al., "Studies on lipid A, the active center of endotoxin—structure–activity relationship." 1989, Drugs Future, 14:645–665.

Hone, et al., "Lipopolysaccharide from an *Escherichia coli* htrB msbB mutant induces high levels of MIP–1A and MIP–1B secretion without inducing TNF–A and IL–1B." 1998, J. Human Virology 1:251–256.

Hone, et al.,"Construction of defined gale mutants of salmonella for use as vaccines." 1987, J. Infect. Dis., 156:167–174.

Hone, et al., "Construction of genetically defined double aro mutants of *salmonella typhi*." 1991, Vaccine 9:810–816.

Huang, et al., "Transscription factor LSF binds two variant bipartite sites within the SV40 late promotor." 1990, Genes Dev., 4:287–298.

Ivey–Hoyle, et al., "Envelope glycoproteins from biologically diverse isolations of immunodeficiency viruses have widely different affinities for CD4." 1991, Proc. Natl. Acad. Sci. USA, 88:512–516.

Jankovic, et al., "Adsorption to aluminum hydroxide promotes the activity of IL–12 as an adjuvant for antibody as well as type 1 cytokine responses to HIV–1 gp120." 1997, J. Immunol., 159:2409–2417.

Johnston and Tomai, "A study of cellular and molecular mediators of the adjuvant action of a nontoxic monophosphoryl lipid A." 1990, Adv. Exp. Med. Biol., 256:567–79.

Jones, et al., "Study of the role of the htrB gene in *Salmonella typhimurium* virulence." 1997, Infect. Immun., 65:4778–4783.

Karow, et al., "Isolation and characterization of the *Escherichia coli* htrB gene, whose product is essential for bacterial viability above 33C in rich media." 1991, J. Bacteriol., 173:741–750.

Karow and Georgopoulos, "Sequencing, mutational analysis, and trasnscriptional regulation of the *Escherichia coli* htrB gene." 1991, Molec. Microbiol., 5:2285–2292.

Karow and Georgopoulos, "Isolation and characterization of the *Escherichia coli* msbB gene, a multicopy suppressor of null mutations in the high–temperature requirement gene htrB." 1992, J. Bacteriol., 174:702–710.

Kass, et al., "Induction of protective host immunity to carcinoembryonic antigen (CEA), a self–antigen in CEA transgenic mice, by immunizing with a recombinant vaccinia–CEA virus." Cancer Research, 59:676–683.

Keddy, et al., "Persistence of antibodies to the *Salmonella typhi* Vi capsular polysaccharide vaccine in South African school children ten years after immunization." 1999, Vaccine, 17:110–113.

Khan, et al., "A lethal role for lipid A in Salmonella infections." 1998, Mol. Microbiology, 29:571–579.

Kirikae, et al., "CD14 is not involved in *Rhodobacter sphaeroides* diphosphoryl lipid A inhibition of tumor necrosis factor alpha and nitric oxide induction by taxol in murine macrophages." 1995, Infect. Immun., 63:486–497.

Kitchens, et al., "Lipopolysaccharide (LPS) Partial structures inhibit responses to LPS in a human macrophage cell line without inhibiting LPS uptake by a CD14–mediated pathway." 1992, J. Exp. Med., 176:485–494.

Kitchens and Munford, "Enzymatically deacylated lipopolysaccharide (LPS) can antagonize LPS at multiple sites in the LPS recognition pathway." 1995, J. Biol. Chem., 270:9904–9910.

Klinman, "Therapeutic applications of CpG–containing oligodeoxynucleotides." 1998, Antisense Nucleic Acid Drug Dev., 8:181–184.

Klugman, et al., "Immunogenicity, efficacy and serological correlate of protection of *Salmonella typhi* Vi capsular polysaccharide vaccine three years after immunization." 1996, Vaccine, 14:435–438.

Kochetkov et al., "Glycosyl esters of necleoside pyrophosphates." 1973, Adv. Carbohydr. Chem. Biochem., 28:307–399.

Koeppen, et al., "Genetically engineered vaccines." 1993, Anal. N.Y. Acad. Sci., 690:244–255.

Koller and Orr, "Cloning and complete sequence of an HLA–A2 gene: analysis of two HLA–A alleles at the nucleotide level." 1985, J. Immunol., 135:2727–2733.

Kotani, et al., "Synthetic lipid A with endotoxic and related biological activities comparable to those of a natural lipid A from *Escherichia coli* re–mutant." 1985, Infect. Immun., 49:225–237.

Kotani, et al., "Immunobiological activities of synthetic lipid A analogs with low endotoxicity." 1986, Infect. Immun., 54:673–682.

Kovach, et al., "Lipid iV$_A$ Inhibits synthesis and release of tumor necrosis factor induced by Lipopolysaccharide in human whole blood ex vivo." 1990, J. Exp. Med., 172:77–84.

Kurane, et al., "Cytokines as an adjuvant to tumor vaccines: efficacy of local methods of delivery." 1997, Ann. Surg. Oncol., 4:579–585.

Lam, et al., "Immunostimulatory, but not antiendotoxin, activity of lipid X is due to small amounts of contaminating N,O–Acylated disaccharide–1–phosphate: invitro and invovo reevaluation of the biological activity of synthetic Lipid X." 1991, Infect. Immun., 59:2351–2358.

Lee, et al., "Mutations of the htrB locus of *Hamemophilus influenzae* nontypable strain 2019 is associated with modifications of lipid A and phosphorylation of the lipo–oligosaccharide." 1995, J. Biol. Chem., 270:27151–27159.

Lee et al., "Transfection of CD14 into 70Z/3 cells dramatically enhances the sensitivity to complexes of lipopolysaccharide (LPS) and LPS binding protein." J. Exp. Med., 175:1697–1705 (1992).

Lee, et al., 1995, In: Abstracts of the American Society for Microbiology, ASM Washington, DC, p. 206 (B–234).

Lee et al., "Molecular cloning and characterization of the nontypeable *Haemophilus influenzae* 2019 rfaE gene required for lipopolysaccharide biosynthesis." 1995, Infect. Immun., 63:818–824.

Li, et al., "Identification of paramyosin as a potential protective antigen against *Brugia malayi* infection in jirds." 1991, Mol. Biochem. Parasitol., 49:315–323.

Liu, et al., "Immunostimulatory CpG Oligodeoxynucleotides enhance the immune response to vaccine strategies involving granulocyte–macrophage colony–stimulating factor." 1998, Blood, 92:3730–3736.

Lofthouse, et al., "Humoral and cellular responses induced by intradermally administered cytokine and conventional adjuvants." 1995, Vaccine 13:1131–1137.

Loppnow, et al., "Lipid A, The immunostimulatory principle of lipopolysaccharides." 1990, Adv. Exp. Med. Biol. 256:561–566.

Lovgren and Morein, "The ioscom: an antigen delivery system with built–in adjuvant." 1991, Molec. Immunol., 28:285–286.

Low, et a., "Lipid A mutant salmonella with suppressed virulence TNFa induction retain tumor–targeting in vivo." 1999, Nature Biotech., 17:37–41.

Macher, 1987, "A convenient synthesis of 2–deoxy–2–[(R)–3–hydroxytetradecanamido]–3–O–(R)–3–hydroxy-tetradecanoyl–a–d–glucopy–ranose 1–phosphate (lipid x)." Carbohydrate Res., 162:79–84.

Mackensen,, et al., "Endotoxin tolerance: regulation of cytokine production and cellular changes in response to endotoxin application in cancer patients." 1992, Eur. Cyto. Net., 3:571–579.

Mackow, et al., "DNA amplification–restricted transcription–translation: rapid analysis of rhesus rotavirus neutralization sites." 1990, Proc. Natl. Acad. Sci. USA, 87:518–22.

Mann, et al., "Sequence of a cysteine–rich galactose–specific lectin of *Entamoeba histolytica*." 1992, Proc. Natl., Acad. Sci. USA, 88:3248–3252.

Manthey, et al., "Modulation of lipopolysaccharide–induced gene expression by *Rhodobacter sphaeroides* lipid A and SDZ 880.431." 1993, Infect. Immun., 61:3518–3526.

Masihi, et al., "Immunobiological activities of nontoxic lipid A: enhancement of nonspecific resistance in combination with dimycolate against viral infection and adjuvant effects." 1986, Int. J. Immunopharmacol., 8:339–345.

May, et al., "The sequence motifs that are involved in SV40 enhancer function also control SV40 late promoter activity," 1987, Nucl. Acids Recs., 15:2445–2461.

Mayordomo, et al., "Therapy of murine tumors with p53 wild–type and mutant sequence peptide–based vaccines." 1996, J. Exp. Med., 183:1357–1365.

McKee and O'Brien, "Investigation of enterohemorrhagic *Escherichia coli* O157:H7 adherence characteristics and invasion potential reveals a new attachment pattern shared by intestinal *E. coli*." 1995, Infect. Immun., 63:2070–2074.

Mitsuya and Broder, "Strategies for antiviral therapy in AIDS." 1987, Nature, 325:773–778.

Moldoveanu, et al., "CpG DNA, a novel immune enhancer for systemic and mucosl immunization with influenza virus." 1998, Vaccine 16:1216–1224.

Morein, "Iscoms." 1990, Vet. Mircrobiol., 23:79–84.

Morishita, et al., "Stable expression of human tissue–type plasminogen activator regulated by B–actin promoter in three human cell lines: HeLa, WI–38 VA13 and KMS–5." 1991, Biochem. Biophys. Acta., 1909:216–222.

Munford, et al., "Biosynthetic radiolabeling of bacterial lipopolysaccharide to high specific activity." 1992, J. Immunol. Methods, 148:115–120.

Munford and Hunter, "Acyloxyacyl hydrolasae, a Leukocyte enzyme that deacylates bacterial lipopolysaccharides, has phospholipase, lysophospholipase, diacylglycerollipase, and acyltransferase in activities in vitro."1992, J. Biol. Chem., 267:10116–10121.

Nash,, et al., "Recombinant cytokines as immunological adjuvants." 1993, Immunol. Cell. Boil., 71:367–379.

Nieminen, et al., "Pneumococcal conjugate vaccination in adults: circulating antibody secreting cell response and humoral antibody responses in saliva and in serum." 1998, Vaccine, 16:630–636.

Noriega, et al., "Construction and characterization of attenuated aroA virG *Shigella flexneri* 2a strain CVD 1203, a prototype live oral vaccine." 1994, Infect. Immun., 62:5168–5172.

O'Gaora, et al., "*Yersinia enterocolitica* aroA mutants as carriers of the B subunit of the *Escherichia coli* heat–labile enterotoxin to the murine immune system." 1990, Micro. Path., 9:105–116.

Odegaard, et al., "Shortened hydroxyacyl chains on lipid A of *Escherichia coli* cells expressing a foreign UDP–N–Acetylglucosamine O–Acyltransferase." 1997, J. Biol. Chem., 272:19688–19969.

Ott, 1994, "Genetic approaches to study *Legionella pneumophila* pathogenicity." FEMS Micro. Rev., 14:161–176.

Palker, et al., "Polyvalent human immunodeficiency virus synthetic immunogen comprised of envelope gp120 T helper cell sites and B cell neutralization epitopes." 1989, J. Immunol., 142:3612–3619.

Pardoll, 1995, "Paracrine cytokine adjuvants in cancer immunotherapy." Annu. Rev. Immunol., 12:339–415.

Pasquini, et al., "Cytokines and costimulatory molecules as genetic adjuvants." 1997, Immnunol. Cell. Biol., 75:397–402.

Perera, et al., "Induction of early gene expression in murine macrophages by synthetic lipid A analogs with differing endotoxic potentials." 1993, Infect. Immun., 61:2015–2023.

Pickard, et al., "Characterization of defined ompR mutants of *Salmonella typhi:* ompR is involved in the regulation of Vi polysaccharide expression." 1994, Infect. Immun., 62:3984–3993.

Pushko, et al., "Replicon–helper systems from attenuated Venezuelan equine encephalitis virus: expression of heterologous genes in vitro and immunization against heterologous pathogens in vivo." 1997, Virology, 239:389–401.

Qureshi, et al., "Chemical reduction of 3–Oxo and unsaturated groups in fatty acids of diphosphoryl lipid A from the Lipopolysaccharide of *Rhodopseudomonas sphaeroides*." 1991, J. Biol. Chem., 266:6532–6538.

Quershi, et al., "Diphosphoryl Lipid A obtained from the nontoxic lipopolysaccharide of *Rhodopseudomonas sphaeroides* is an endotoxin antagonist in mice." 1991, Infect. Immun., 59:441–444.

Quershi, et al., "Structure of the monophosphoryl lipid A moiety obtained from the Lipopolysaccharide of *Chlamydia trachomatis*." 1997, J. Biol. Chem., 272:10594–10600.

Raetz, "Biochemistry of Endotoxins." 1990, Ann. Rev. Biochem., 59:129–170.

Raetz, et al., "Isolation and characterization of eight lipid A precursors from a 3–deoxy–D–manno–octyloxonic Acid–deficient mutant of *Salmonella typhimurium*." 1985, J. Bio. Chem., 260:16080–16088.

Raetz, "Bacterial Endotoxins: Extraordinary Lipids that Activate Eucaryotic Signal Transduction." 1993, J. Bacteriology, 175:5745–5753.

Reitz, et al., "Partial envelope sequences from some of the earliest isolates of HIV–1." 1994, AIDS Res. Hum. Retroviruses, 10:621–623.

Rennels, et al., "Safety and immunogenicity of heptavalent pneumococcal vaccine conjugated to $CRM_{197}$ in United States infants." 1998, Pediatrics, 191:604–611.

Rick et al., "Lipid A mutants of Salmonella typhimurium." 1997, J. Biol. Chem., 252:4904–4912.

Rick and Osborne, "Lipid A mutants of Salmonella typhimurium." 1997, J. Biol. Chem., 252:4895–4903.

Rietschel, et al., "Bacterial endotoxin: molecular relationships of structure to activity and function." 1994 FASEB Journal, 8:217–225.

Robbins and Robbins, "Reexamination of the protective role of the capsular polysaccharide (Vi antigen) of Salmonella typhi." 1984, J. Infec. Dis., 159:436–449.

Roberts, et al., "Recombinant P.69/pertactin: immunogenicity and protection of mice against Bordetella pertussis infection." 1992, Vaccine, 29:43–48.

Rose, et al., "Agonistic and antagonistic activities of bacterially derived Rhodobacter sphaeroides Lipid A: comparison with activities of synthetic material of the proposed structure and analogs." 1995, Infect. Immun., 63:833–839.

Rotondaro, et al., "Efficiency of different viral promoters in directing gene expression in mammalian cells: effect of 3'–untranslated sequences." 996, Gene, 168:195–198.

Russell, et al., "Effective immunization against cutaneous Leishmaniasis with defined membrane antigens reconstituted into liposomes." 1998, J. Immunol., 140:1274–78.

Sadoff, et al., "Oral Salmonella typhimurium vaccine expressing circumsporozoite protein protects against malaria." 1988, Science, 240:336–337.

Saha, et al., "Monophosphoryl lipid A stimulated up–regulation of nitric oxide synthase and nitric oxide release by human monocytes in vitro." 1997, Immunopharmacol., 37:175–84.

Sansonetti, et al., "Plasmid–mediated invasiveness of shigella–like Escherichia coli." 1982, Ann. Microbiol., (Inst. Pasteur), 132A:351–355.

Sasaki, et al., "Monophosphoryl lipid A enhances both humoral and cell–mediated immune responses to DNA vaccination against human immunodeficiency virus type 1." 1997, Infection and Immunity, 63:3520–3528.

Schnaitman and Klena, "Genetics of lipopolysaccharide biosynthesis in enteric bacteria." 1993, Microbiol. Rev., 57:655–682.

Schneerson, et al., "Evaluation of monphosphoryl lipid A (MPL) as an adjuvant." 1991, J. Immuno., 147:2136–2140.

Seppala and Makela, "Adjuvant effect of bacterial LPS and/or alum precipitation in responses to polysaccharide and protein antigens." 1994, Immunol., 53:826–836.

Shirodkar, et al., "Aluminum compounds used as adjuvants in vaccines." 1990, Pharm. Res., 7:1282–1288.

Shnyra, et al., "Role of the physical state of salmonella lipopolysaccharide in expression of biological and endotoxic properties." 1993, Infection and Immunity, 61:5351–5360.

Shoemaker, et al., "cDNA cloning and functional expression of the Schistosoma mansoni protective antigen triose–phosphate isomerase." 1992, Proc. Natl. Acad. Sci. USA, 89:1842–46.

Sjolander, et al., "ISCOMs: an adjuvant with multiple functions." 1998, J. Leukoc. Biol., 64:713–723.

Somerville, et al., "A novel Escherichia coli Lipid A mutant that produces an anti–inflammatory lipopolysaccharide." 1996, J. Clin. Invest., 97:359–365.

Spetzler, et al., ∂A novel strategy for the synthesis of the cysteine–rich protective antigen of the malaria merozoite surface protein (MSP–1) 1994, Int. J. Pept. Prot. Res., 43:351–58.

Stauffer, et al., "Characterization of the gcv control region from Escherichia coli." 1994, J. Bact., 176:6159–6164.

Sunshine, et al., "Mutation of the htrB gene in a virulent Salmonella typhimurium strain by intergeneric transduction: strain construction and phenotypic characterization." 1997, J. Bacteriology, 179:5521–5533.

Tabatabai, et al., "Monophosphoryl lipid A–induced immune enhancement of Brucella abortus salt–extractable protein and lipopolysaccharide vaccines in BALB/c mice." 1992, Am. J. Bet. Res., 53:1900–1908.

Tagliabue and Boraschi, "Cytokines as vaccine adjuvants: interleukin 1 and its synthetic peptide 163–171." 1993, Vaccine, 11:594–595.

Taylor, et al., "Development of a live, oral, attenuated vaccine against el tor cholera." 1994, J. Infect. Dis., 170:1518–1523.

Theofan, et al., "An amino–terminal fragment of human lipopolysaccharide–binding protein retains lipid A binding but not CD14–stimulatory activity." 1994, J. Immunol., 152:3623–3629.

Thomsen, et al., "Promoter–regulatory region of the major immediate early gene of human cytomegalovirus." 1984, Proc. National Acad. Sci., 81:659–663.

Tobias et al., "Identification of a lipid A binding site in the acute phase reactant lipopolysaccharide binding protein." 1989, J. Biol. Chem., 264:10867–71.

Tobias et la., "A family of lipopolysaccharide binding proteins involved in responses to gram–negative sepsis." 1988, J. Biol. Chem., 263:13479–81.

Tohme et al., "Moesin functions as a lipopolysaccharide receptor on human monocytes." 1999, Infect. Immun., 67:3215–3220.

Topham, et al., "A synthetic peptide from the third hypervariable region of major histocompatibility complex class II B chain as a vaccine for treatment of experimental autoimmune encephalomyelitis." 1994, Proc. Natl. Acad. Sci. USA, 91:8005–8009.

Traquina, et al., "MF59 adjuvant enhances the antibody response to recombinant Hepatitis B surface antigen vaccine in primates." 1996, J. Infect. Dis., 174:1168–75.

Ugozzoli, et al., "Intranasal immunication of mice with herpes simplex virus type 2 recombinant gD2: the effect of adjuvants on mucosal and serum antibody responses." 1998, Immunol., 93:563.

Ulmer, et al., "Biological activity of synthetic, phosphonooxyethyl analogs of lipid A and lipid A partial structures." 1992, Infect. Immun., 60:3309–3314.

Ulmer, et al., "Modulation of endotoxin–induced monokine release in human monocytes by lipid A partial structures that inhibit binding of$^{125}$I–Lipopolysaccharide." 1992, Infect. Immuno., 60:5145–5152.

Van Dervort et al., "Antagonism of lipopolysaccharide–induced priming of human neutrophils by lipid A analogs." 1992, J. Immunol., 149:359–366.

Verhasselt, et al., "Bacterial lipopolysaccharide stimulates the production of cytokines and the expression of costimulatory molecules by human peripheral blood dendritic cells." 1997, J. Immunol., 158:2919–2925.

Verma, et al., "Adjuvant effects of liposomes containing lipid A: enhancement of liposomal antigen presentation and recruitment of macrophages." 1992, Infect. Immun., 60:2438–2444.

Vordemeier, et al., "Synthetic delivery system for tuberculosis vaccines: immunological evaluation of the *M. tuberculosis* 38 kDa protein entrapped in biodegradable PLG microparticles." 1995, Vaccine 13:1576–1582.

Waldor, et al., "Emergence of a new cholera pandemic: molecular analysis of virulence determinants in *Vibrio cholerae* O139 and development of a live vaccine prototype." 1994, J. Infect. Dis., 170:278–283.

Wang et al., "Suppressive effect of lipid A partial structures on lipopolysaccharide or lipid A–induced release of interleukin 1 by human monocytes." 1990, FEMS Micro. Immuno., 2:179–186.

Wang et al., "Inhibition of endotoxin–induced interleukin–6 production by synthetic lipid A partial structures in human peripheral blood mononuclear cells." 1991, Infect. Immun., 59:4655–64.

Weisburg, et al., "Characterization of the MN gp120 HIB–2 Vaccine: antigen binding to alum." 1995, Pharm. Res., 12:1439–1446.

Wloch, et al., "The influence of DNA sequence on the immunostimulatory properties of plasmid DNA vectors." 1998, Hum. Gene. Therap., 9:1439–1447.

Wu, et al., "Expression of immunogenic epitopes of hepatitis B surface antigen with hybrid flagellin proteins by a vaccine strain of salmonella." 1989, Proc. Natl. Acad. Sci USA, 86:4726–30.

Wu, et al., "Induction of mucosal and systemic responses against human immunodeficiency virus type 1 glycoprotein 120 in mice after oral immunication with a single dose of a salmonella–HIV vector." 1997, AIDS Res. Human Retroviruses, 13:1187–1194.

Yamamoto, et al., "Enteroadhesion fimbriae and enterotoxin of *Escherichia coli:* genetic transfer to a streptomycin–resistant mutant of the gale oral–route live–vaccine *Salmonella typhi* Ty21a." 1985, Infect. Immun., 50:925–28.

Zhou and Huang, L., "Monophosphoryl lipid A enhances specific CTL induction by a soluble protein antigen entrapped in liposomes." 1993, Vaccine, 11:1139–1144.

Zuckerman and Qureshi, "In vivo inhibition of lipopolysaccharide–induced lethality and tumor necrosis factor synthesis by *Rhodobacter sphaeroides* diphosphoryl lipid A is dependent on corticosterone induction." 1992, Infect. Immun., 60:2581–2587.

Lidgate and Byars, 1995, In: Vaccine Design. The Subunit and Adjuvant Approach. Powell and Newman (ed), Plenum Press, NY, NY, p. 313–325.

Makela and Stocker, 1984, In:Handbook of Endotoxin vol. 1, Elsevier Biomedical Press, Amsterdam, Rietschel (ed.), p. 59–137.

Ott, et al., 1995, In: Vaccine Design. The Subunit and adjuvant approach. Powell and Newman (eds), Plenum Press, NY, NY, p. 277–296.

Rimmelzwaan and Osterhaus, 1995, In: Vaccine Design. The subunit and Adjuvant Approach, Powell and Newman (eds) Plenum Press, NY, NY, p. 543–559.

Ulrich and Myers, 1995, In: Vaccine Design. The Subunit and Adjuvant Approach. Powell and Newman (ed), Plenum Press, NY, NY, p. 495–525.

Vogel and Powell, 1995, In:Vaccine Design, The Subunit and Adjuvant Approach. Powell and Newman (eds), Plenum Press, NY, NY, p. 141–229.

Whitley, et al., New Generation Vaccines, p. 825–854.

Wong et al., 1994, Enzymes in Synthetic Organic Chemistry, Pergamon Press, vol. 12, pp. 256–264.

* cited by examiner

ADJUVANT COMPRISING A LIPOPOLYSACCHARIDE ANTAGONIST

CROSS-REFERENCE TO RELATED APPLICATIONS

This application is filed under the provisions of 35 U.S.C. §371 and claims the priority of International Patent Application No. PCT/US00/27402 filed Oct. 4, 2000, which in turn claims priority of U.S. Provisional Application No. 60/157,635 filed on Oct. 4, 1999 and No. 60/192,650 filed on Mar. 27, 2000.

1. FIELD OF THE INVENTION

The invention provides a novel vaccine adjuvant comprising lipopolysaccharide (LPS) antagonist, and use of the same in vaccine preparations and methods of vaccinating a subject comprising a vaccine antigen and a pharmaceutically active amount of an LPS antagonist.

2. BACKGROUND OF THE INVENTION

2.1 General Properties of Adjuvants

An adjuvant is a compound that, when combined with a vaccine antigen, increases the immune response to the vaccine antigen over that induced by the vaccine antigen alone. Strategies that promote antigen immunogenicity include those that render vaccine antigens particulate, polymerize vaccine antigens, emulsify vaccine antigens, encapsulate vaccine antigens, increase host innate cytokine responses, or target vaccine antigens to antigen presenting cells (Nossal, 1999, In: Fundamental Immunology. Paul (Ed.), Lippincott-Raven Publishers, Philadelphia, Pa.; Vogel and Powell, 1995, In: Vaccine Design. The Subunit and Adjuvant Approach. Powell and Newman (Eds.), Plenum Press, NY, N.Y. p. 141). Because of the essential role adjuvants play in improving the immunogenicity of vaccine antigens, the use of adjuvants in the formulation of vaccines has been virtually ubiquitous (Nossal, 1999, supra; Vogel and Powell, 1995, supra; see also PCT publication WO 97/18837, the teachings of which are incorporated herein by reference).

A compendium of adjuvants with know immunomodulatory properties is available (Vogel and Powell, 1995, supra). Examples of well-known adjuvants include Freund's adjuvant (Vogel and Powell, 1995, supra), MF59 (Vogel and Powell, 1995, supra; Ott, et al., 1995, In; Vaccine Design. The subunit and adjuvant approach. Powell and Newman (Eds.), Plenum Press, NY, N.Y. p.277; Traquina, et al., 1996, J. Infect. Dis., 174:1168; Ott, et al., 1995, Pharm. Biotechnol., 6:277), SAF-1 (Vogel and Powell, 1995, supra), polylactide co-glycolide encapsulation (PLG; (Vogel and Powell, 1995, supra; Eldridge, et al., 1991, Infect. Immun., 59:2978; Eldridge, et al., 1993, Semin. Hematol., 30:16; Vordermeier, et al., 1995, Vaccine 13:1576; Ugozzoli, et al., 1998, Immunol., 93:563), aluminium hydroxide/phosphate ("Alum"; (Vogel and Powell, 1995, supra; Edelman, 1980, Rev. Infect. Dis., 2:370; Seppala and Makela, 1984, Immunol., 53:827; Shirodkar, et al., 1990, Pharm Res., 7:1282; Weissburg, et al., 1995, Pharm. Res., 12:1439), and immune-stimulating complexes ("ISCOMs"; Vogel and Powell, 1995, supra; Rimmelzwaan and Osterhaus, 1995, In: Vaccine Design. The Subunit and Adjuvant Approach. Powell and Newman (Eds.), Plenum Press, NY, N.Y. p.543; Sjolander, et al., 1998, J. Leukoc. Biol., 64:713; Morein, 1990, Vet. Microbiol., 23:79; Lovgren and Morein, 1991, Molec. Immunol., 28:285).

A more recent adjuvant strategy has been to use purified recombinant cytokines as adjuvants (Vogel and Powell, 1995, supra). Cytokines that have been employed in this fashion include IL-1a, TNFa, IL-2, IL4, IL-6, IL-12, interferon-gamma (IFN-γ), and granulocyte monocyte colony stimulating factor (GM-CSF; Nossal, 1999, supra; Vogel and Powell, 1995, supra; Nash, et al., 1993, Immunol. Cell. Biol., 71:367; Pardoll, 1995, Annu. Rev. Immunol., 13:399; Kurane, et al., 1997, Ann. Surg. Oncol., 4:579; Tagliabue and Boraschi, 1993, Vaccine, 11:594; Lofthouse, et al., 1995, Vaccine, 13:1131; Pasquini, et al., 1997, Immunol. Cell. Biol., 75:397; Jankovic, et al., 1997, J. Immunol., 159:2409).

The advent of nucleic acid vaccines has enabled new avenues in the field of adjuvant development. This includes the use of nucleic acid vaccines that encode cytokines, such as IL-4, IFN-γ and GM-CSF, in addition to the vaccine antigen (Pasquini, et al., 1997, supra) and nucleic acid vaccines that encode co-stimulatory molecules such as CD80 (also known as B7.1), in addition to the vaccine antigen (Pasquini, et al., 1997, supra).

Although there is no single mechanism of adjuvant action, an essential characteristic of adjuvants is their ability to significantly increase the level of immunity to a vaccine antigen over the level of immunity induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra).

Several adjuvants are derived from bacterial products. Bacteria are composed of a diverse array of biologically active components that have proven adjuvant activity, including porins, cholera toxin (also called "C"), heat-labile toxin of enterotoxigenic E. coli (also called LT), muramyl dipeptide, lipoarabinomannans ("LAM"), lipid A, and monophosphoryl-lipid A (Nossal, 1999, supra; Vogel and Powell, 1995, supra; Lidgate and Byars, 1995, In: Vaccine Design. The Subunit and Adjuvant Approach. Powell and Newman (Eds.), Plenum Press, NY, N.Y. p.313; Ulrich and Myers, 1995, In: Vaccine Design. The Subunit and Adjuvant Approach. Powell and Newman (Eds.), Plenum Press, NY, N.Y. p.495). In addition, unmethylated CpG DNA sequences, which are expressed by bacteria or made synthetically, have been shown to possess potent immunostimulatory properties (Davis, et al., 1998, J. Immunol., 160:870; Klinman, 1998, Antisense Nucleic Acid Drug Dev., 8:181; Liu, et al., 1998, Blood, 92:3730; Wloch, et al., 1998, Hum. Gene. Therap., 9:1439; Brazolot-Milla, et al., 1998, Proc. Natl. Acad. Sci. USA, 95:15553; Moldoveanu, et al., 1998, Vaccine, 16:1216). Inclusion of such sequences in nucleic acid vaccines is thought to play a key role in the immunogenicity of DNA vaccines (Davis, et al., 1998, supra; Klinman, 1998, supra; Liu, et al., 1998, supra; Wloch, et al., 1998, supra; Brazolot Milla, et al., 1998, supra; Moldoveanu, et al., 1998, supra).

2.2 Bacterial LPS and Lipid A

LPS (lipopolysaccharide), also referred to as "endotoxin", is the major surface component of gram negative bacteria. Under normal conditions, LPS is inserted in the outer surface of the outer membrane of gram negative bacteria (Schnaitman and Klena, 1993, Microbiol. Rev., 57:655;

Makela and Stocker, 1984, In: Handbook of Endotoxin volume 1, Elsevier Biomedical Press, Amsterdam, Rietschel (Ed.), pp. 59–137). Complete or "smooth" LPS is composed of three main domains called lipid A, the O-antigen (also called the O-polysaccharide) and the core region, which creates an oligosaccharide link between lipid A and the O antigen (Schnaitman and Klena, 1993, supra; and Makela and Stocker, 1984, supra). The O-antigen is composed of oligosaccharide repeat units. The structure and number of these repeats varies depending on the bacterial species and growth conditions, typically ranging from one to fifty repeats (Schnaitman and Klena, 1993, supra; and Makela and Stocker, 1984, supra). Some bacterial generi, such as Neisseria spp., produce LPS that has low numbers of O-antigen repeats and therefore is referred to as lipooligosaccharide (LOS) simply to reflect this fact (Schnaitman and Klena, 1993, supra; and Makela and Stocker, 1984, supra).

The biologically active component of LPS is lipid A (Rietschel, et al., 1994, FASEB J., 8:217; Verma, et al., 1992, Infect. Immun., 60:2438; Alving, 1991, J. Immunol. Meth., 140:1; Alving and Richards, 1990, Immunol. Lett., 25:275; Richard, et al., 1988, Infect. Immun., 56:682. Activity analysis of lipid A biosynthesis precursors or synthetic intermediates showed that various elements of lipid A are essential for pyrogenicity (Rietschel, et al., 1994, supra; Raetz, et al., 1985, J Biol. Chem., 260:16080). Lipid X and lipid IVa are completely non pyrogenic precursor forms of lipid A (Wang, et al., 1991, Infect. Immun., 59:4655; Ulmer, et al., 1992, Infect. Immun., 60:145; Kovach, et al., 1990, J. Exp. Med., 172:77).

Lipid X is a monosaccharide precursor of lipid A (Rietschel, et al., 1994, supra). Lipid IVa, a tetraacyl precursor of lipid A, is interesting in that it retains the ability to bind to host cell surfaces but has no pyrogenicity, suggesting that binding to host cell surfaces per se does not impart this biological property (Wang, et al., 1991, supra; Ulmer, et al., 1992, supra; Kovach, et al., 1990 supra).

2.3 The Genetics of Lipid A Biosynthesis

The genetics of lipid A biosynthesis are well described (e.g., Raetz, et al., 1985, supr,. Raetz, 1990, Ann. Rev. Biochem., 59:129). The majority of mutations that prevent the biosynthesis of lipid A, such as mutations in the IpxA, lpxB, kdsA, kdsB, and kdtA genes, are lethal as the biosynthesis of lipid A is essential for cell survival (Rick, et al., 1977, J. Biol. Chem., 252:4904; Rick and Osborne, 1977, J. Biol. Chem., 252:4895; Raetz, et al., 1985, supra; Raetz, et al., 1990, supra; Raetz, et al., 1993, supra; Schnaitman and Klena, 1993, supra). For the most part, therefore, analysis of these genes has involved the use of temperature-sensitive mutants, which only display null phenotypes under non-permissive conditions (Rick, et al., 1977, supra; Rick and Osborne, 1977, supra; Raetz, et al., 1985, supra; Raetz, et al., 1990, supra; Raetz, et al., 1993, supra; Schnaitman and Klena, 1993, supra). When grown under non permissive conditions, lpxA, kdsA, kdsB, and kdtA mutants accumulate non-pyrogenic precursor forms of LPS (to about 50% of the total LPS), such as lipid X or lipid IVa.

There is now evidence that mutations in htrB and msb may influence the biosynthesis of lipid A (Karow, et al., 1991, J. Bacteriol., 173:741; Karow and Georgopoulos, 1992, J. Bacteriol., 174:702). These mutants are temperature sensitive and LPS isolated from these mutants stains less intensely on silver-stain gels (Karow and Georgopoulos, 1992, supra). The basis for the temperature-sensitive growth phenotype of the htrB and msb mutants has remained cryptic (Karow and Georgopoulos, 1992, supra). There was speculation that these mutants produce defective lipid A precursors (Karow and Georgopoulos, 1992, supra). This was based on the observation that ammonium cationic compounds enabled these mutants to grow in non permissive temperatures (Karow and Georgopoulos, 1992, supra). These investigators proposed that the ammonium cationic compounds influenced the intermolecular interaction between LPS molecules in the outer membrane. This observation is supported by a report showing that an htrB mutant of *Haemophilus influenzae* produces modified LOS structures (Lee, et al., 1995, Infect. Immun., 63:818; Lee, et al., 1995, In: Abstracts of the American Society for Microbiology, ASM Washington D.C., p.206 (B-234)). Later studies showed direct evidence that htrB and msb mutants could produce substantially pure non-pyrogenic LPS (see PCT International Publication Nos. WO 97/18837 and WO 99/15162, the teachings of which are incorporated herein by reference).

Other lipid A precursor structures isolated from *E. coli* mutants that are defective in the biosynthesis of lipid A are described in Raetz, et al., 1985, supra; Kovach, et al., 1990, J. Exp. Med., 172:77; Golenbock, et al., 1991, J. Biol. Chem., 266:19490; Golenbock, et al., 1988, Antimicrob. Agents Chemother., 32:37; Clementz, et al., 1996, J. Biol. Chem., 271:12095; Clementz, et al., 1997, J. Biol. Chem., 272:10353; Garrett, et al., 1998, J. Biol. Chem., 273:12457; Kitchens, et al., 1992, J. Exp. Med., 176:485; Kitchens, and Munford, 1995, J. Biol. Chem., 270:9904; Munford and Hunter, 1992, J. Biol. Chem., 267:10116; Rietschel, et al., 1994, supra; Ulmer, et al., 1992, Infect. Immun., 60:5145; Ulmer, et al., 1992, Infect. Immun., 60:3309; Wang, et al., 1990, FEMS Micro. Immunol., 2:179; Wang, et al., 1991, Infect. Immun., 59:4655 64.

Synthetic lipid A partial structures are described in Wang, et al., 1990, FEMS Microbiol. Immunol., 2:179; Golenbock, et al., 1991, J. Biol. Chem., 266:19490; Ulmer, et al., 1992, Infect. Immun., 60:3309; Ulmer, et al., 1992, Infect. Immun., 60:5145; Perera, et al., 1993, Infect. Immun., 61:2015; Rietschel, et al., 1994, supra. *Rhodobacter sphaeroides* naturally produces an unusual diphosphoryl-lipid A structure (hereafter referred to as RsDPLA) that lacks pyrogenic activity (Qureshi, et al., 1991, J. Biol. Chem., 266:6532; Qureshi, et al., 1991, Infect. Immun., 59:441; Zuckerman and Qureshi, 1992, Infect. Immun., 60:2581; Kirikae, et al., 1995, Infect. Immun., 63:486; Qureshi, et al., 1997, J. Biol. Chem., 272:10594).

Through these studies a number of lipid A partial structures have been identified that lack pyrogenic activity and are LPS antagonists (i.e., they effectively block the pyrogenic activity of LPS from gram negative bacteria, e.g., *E. coli* LPS) including lipid X, tetraacyl-lipid A (LA4), pentaacyl-lipid A (LAS), and RsDPLA (Kovach, et al., 1990, supra; Golenbock, et al., 1991, supra; Golenbock, et al., 1988, supra; Kitchens, et al., 1992, supra; Kitchens and Munford, 1995, supra; Munford and Hunter, 1992, supra; Rietschel, et al., 1994, supra; Ulmer, et al., 1992, supra; Ulmer, et al., 1992, supra; Wang, et al., 1990, supra; Wang, et al., 1991, supra; Qureshi, et al., 1991, supra; Qureshi, et al., 1991, supra; Zuckerman and Qureshi, 1992, supra; Kirikae, et al., 1995, supra; Qureshi, et al., 1997, supra).

More recently, *E. coli* msbB mutants have been shown to produce LAS and LPS preparations isolated from *E. coli* msbB mutants were shown to possess LPS antagonist activity (Clementz, et al., 1997, supra; Somerville, et al., 1996, J. Clin. Invest., 97:359). Similarly, other investigators have shown that *E. coli* hirB and msbB mutants (Clementz, et al., 1996, supra; Clementz, et al., 1997, supra; Hone, et al., 1998, J. Human Virol., 1:251), Salmonella htrB mutants (Sunshine, et al., 1997, J. Bacteriol., 179:5521; Jones, et al., 1997, Infect. Immun., 65:4778), and msbB mutants (Low, et al., 1999, Nature Biotech., 17:37; Khan, et al., 1998, Mol. Microbiol., 29:571), and Haemophilus htrB mutants (Lee, et al., 1995, J. Biol. Chem., 270:27151) produce defective lipid A structures, predominated by LA4 and LA5, that are non pyrogenic and display LPS antagonist activity.

These findings also provided compelling evidence that the products of the htrB and msbB genes play a central role in the final steps of lipid A biosynthesis in gram negative bacteria that produce LAS or hexaacyl-lipid A structures, such as Escherichia spp., Shigella spp., Salmonella spp., Campylobacter spp., Neisseria spp., Haemophilus spp., Aeromonas spp., Francisella spp., Yersinia spp., Klebsiella spp., Bordetella spp., Legionella spp., Corynebacterium spp., Citrobacter spp., Chlamydia spp., Brucella spp., Pseudomonas spp., Helicobacter spp., and Vibrio spp. (Clementz, et al., 1997, supra; Somerville, et al., 1996, supra; Lee, et al., 1995, supra; Low, et al., 1999, supra; Khan, et al., 1998, supra; Sunshine, et al., 1997, supra; Jones, et al., 1997, supra).

Despite the diverse number of lipid A structures that have been identified that are non pyrogenic and display LPS antagonist activity, a consistent finding that emerged from the above described research effort was that lipid A precursors and partial structures that possess LPS antagonist activity (i.e., those produced by *E. coli* mutants and those made synthetically) failed to reproducibly display an effective adjuvant activity (Rietschel, et al., 1994, supra; Kotani, et al., 1986, Infect. Immun., 54:673; Hamann, et al., 1998, Int. J. Food Microbiol., 41:141; Loppnow, et al., 1990, Adv. Exp. Med. Biol., 256:561). In one instance the putative immunostimulatory activity of the LPS antagonist lipid X was subsequently shown to be due to the presence of a contaminant in the preparation. Once the contaminant was completely eliminated the immunostimulatory activity was completely lost (Lam, et al., 1991, Infect. Immun., 59:2351). Other reports claiming immunostimulatory activity in LPS antagonists are now thought to be due to contaminating protein in the LPS antagonist preparations (Hogan and Vogel, 1987, J. Immunol., 139:3697; Hogan and Vogel, 1988, J. Immunol., 141:4196).

Notwithstanding the above disappointing revelation, some lipid A structures that display markedly reduced pyrogenicity, were shown to retain adjuvant activities; a well known example in this category is monophosphoryl-lipid A (referred to herein as MPLA; Saha, et al., 1997, Immunopharmacol., 37:175–84; Hagen, et al., 1997, J Chromatogr., 767:53; Ulrich and Myers, 1995, Pharm. Biotechnol., 6:495; Zhou and Huang, L., 1993, Vaccine, 11:1139; Tabatabai, et al., 1992, Am. J. Vet. Res., 53:1900; Schneerson, et al., 1991, J. Immunol., 147:2136; Masihi et al., 1986, Int. J. Immunopharmacol., 8:339; Johnson and Tomai, 1990, Adv. Exp. Med. Biol., 256:567–79). However, while MPLA displays substantially reduced pyrogenic activity, it induces modest levels of pyrogenic cytokines and does not possess LPS antagonist activity (Saha, et al., 1997, supra; Hagen, et al., 1997, supra; Ulrich and Myers, 1995, supra; Zhou and Huang, 1993, supra; Tabatabai, et al., 1992, supra; Schneerson, et al., 1991, supra; Masihi, et al., 1986, Int. J. Immunopharmacol. 8:339; Johnson and Tomai, 1990, supra).

Accordingly, the prior art teaches us that LPS antagonists, when used as highly purified preparations, display poor adjuvant properties compared to other widely used adjuvants such as those described in Section 2 above. That is, the prior art does not provide LPS, lipid A or derivatives thereof that are effective LPS antagonists and adjuvants, and lack pyrogenic activity.

3. SUMMARY OF THE INVENTION

The invention relates to methods and compositions comprising an adjuvant which is both an LPS antagonist and is non-pyrogenic. In a preferred embodiment, the non-pyrogenic LPS antagonist adjuvant is isolated from a gram negative bacterial strain that contains at least one mutation in at least one of the htrB and msbB genes.

In one aspect, the invention features an adjuvant comprising an LPS antagonist, wherein said LPS antagonist is isolated from a gram negative bacterium that is defective in at least one of the msbB or htrB genes. In one embodiment, the LPS antagonist has reduced pyrogenicity. In a preferred embodiment, the LPS antagonist has substantially reduced pyrogenicity. In a more preferred embodiment, the LPS antagonist in non-pyrogenic. In a preferred embodiment, pyrogenicity is determined by measuring the levels of indicators of pyrogenicity or inflammation, such as, for example, IL-1$\beta$, IL-6 or TNF$\alpha$, in a cell, extracellular medium, or a subject. In a most preferred embodiment, the LPS antagonist elicits no detectable TNF$\alpha$ activity when contacted with a cell or administered to a subject.

The LPS antagonist may comprise an LPS derivative or a fragment thereof (e.g., a precursor component or derivative thereof), such as a lipid A precursor structure selected from the group consisting of lipid X, tetraacyl-lipid A (LA4), pentaacyl-lipid A (LAS), or a *Rhodobacter sphaeroides* diphosphoryl-lipid A structure (RsDPLA). The LPS antagonist can be purified from a gram negative bacteria is selected from the group consisting of Escherichia spp., Shigella spp., Salmonella spp., Campylobacter spp., Neisseria spp., Haemophilus spp., Aeromonas spp., Francisella spp., Yersinia spp., Klebsiella spp., Bordetella spp., Legionella spp., Corynebacterium spp., Citrobacter spp., Chlamydia spp., Brucella spp., Pseudomonas spp., Helicobacter spp., and Vibrio spp.

In another embodiment, the gram negative bacterium defective in at least one of the msbB or htrB genes is also defective in at least one of the kdsA, kdsB, kdtA, lpxA, lpxB, lpxC lpxD or ssc genes.

In another embodiment, the invention provides a pharmaceutical preparation comprising a vaccine antigen, a pharmaceutically effective amount of an LPS antagonist, isolated from a gram negative bacterium that is defective in at least one of the msbB or htrB genes, and a pharmaceutically acceptable carrier. The vaccine antigen may be any vaccine antigen, such as e.g., a polysaccharide, a protein or a nucleic acid. In an embodiment of the invention, the vaccine antigen is derived from a viral pathogen selected from the group consisting of orthomyxoviruses, retroviruses, herpesviruses, lentiviruses, rhabdoviruses, picornoviruses, poxviruses, rotavirus and parvoviruses. Exemplary antigens are influenza virus, RSV, EBV, CMV, herpes simplex virus, human immunodeficiency virus, rabies, poliovirus and vaccinia, human immunodeficiency virus antigens Nef, p24, gp120, gp41, Tat, Rev, and Pol; T cell and B cell epitopes of gp120; the hepatitis B surface antigen; rotavirus antigens, such as VP4 and VP7; influenza virus antigens such as hemagglutinin or nucleoprotein; and herpes simplex virus thymidine kinase.

In another embodiment the vaccine is derived from a bacterial pathogen selected from the group consisting of Mycobacterium spp., *Helicobacter pylori*, Salmonella spp., Shigella spp., *E. coli*, Rickettsia spp., Listeria spp., *Legionella pneumoniae*, Pseudomonas spp., Vibrio spp., and *Borellia burgdorferi*. Exemplary vaccine antigens useful in the practice of the invention are the capsular polysaccharide of *Neisseria meningitis*; the Vi polysaccharide of *Salmonella enterica* serovar *typhi; Shigella sonnei* form 1 antigen; the O-antigen of *V. cholerae* Inaba strain 569; cholera toxin of *V. cholerae*; TCP of *V. cholera*; CFA/I fimbrial antigen of enterotoxigenic *E. coli*; the heat-labile toxin of *E. coli*; pertactin of *Bordetella pertussis*; adenylate cyclase-hemolysin of *B. pertussis*, and fragment C of tetanus toxin of *Clostridium tetani*.

In another embodiment of the invention the vaccine antigen is derived from a parasitic pathogen selected from the group consisting of Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp. Exemplary parasitic vaccine antigen useful in the practice of the invention are the circumsporozoite antigen of *P. berghei*, the circumsporozoite antigen of *P. falciparum*; the merozoite surface antigen of Plasmodium spp.; the galactose specific lectin of *Entamoeba histolytica*; gp63 of Leishmania spp.; paramyosin of *Brugia malayi*; the triose-phosphate isomerase of *Schistosoma mansoni*; the secreted globin-like protein of *Trichostrongylus colubriformis*; the glutathione-S-transferase of *Frasciola hepatica, Schistosoma bovis* and *S. japonicum*; and KLH of *Schistosoma bovis*.

In additional embodiments of the invention the vaccine antigen is derived from a tumor antigen selected from the group consisting of prostate specific antigen, TAG-72, carcinoembrionic antigen (CEA), MAGE-1, tyrosinase, and mutant p53 antigen; the CD3 receptor on T cells; an autoimmune antigen; or the IAS β chain. Alternatively, the invention can be practiced with a vaccine antigen such as an immuno-stimulatory molecule selected from the group consisting of M-CSF, GM-CSF, IL-2, IL-4, IL-5, IL-6, IL-10, IL-12 and IFN-γ.

An another aspect, the invention features combination therapies, comprising a pharmaceutical composition containing the LPS antagonist together with other agents that enhance the activity of the LPS antagonist (e.g., by increasing its adjuvant or antagonist activities or promoting stabilization of the LPS antagonist or other components of the pharmaceutical composition) or minimize deleterious effects of the LPS antagonist.

In another aspect, the invention features methods for preparing and using an adjuvant as described herein comprising an LPS antagonist, wherein said LPS antagonist is isolated from a gram negative bacterium that is defective in at least one of the msbB or htrB genes.

In another aspect, the invention features methods for preparing and using a vaccine comprising a vaccine antigen and a pharmaceutically effective amount of an LPS antagonist isolated from a gram negative bacterium that is defective in at least one of the msbB or htrB genes, and a pharmaceutically acceptable carrier.

Other features and advantages of the invention will be apparent from the following Figures, Detailed Description, Examples and from the Claims.

4. BRIEF DESCRIPTION OF THE DRAWINGS

5. DETAILED DESCRIPTION OF THE INVENTION

5.1 Overview of the Invention

Figure 1:
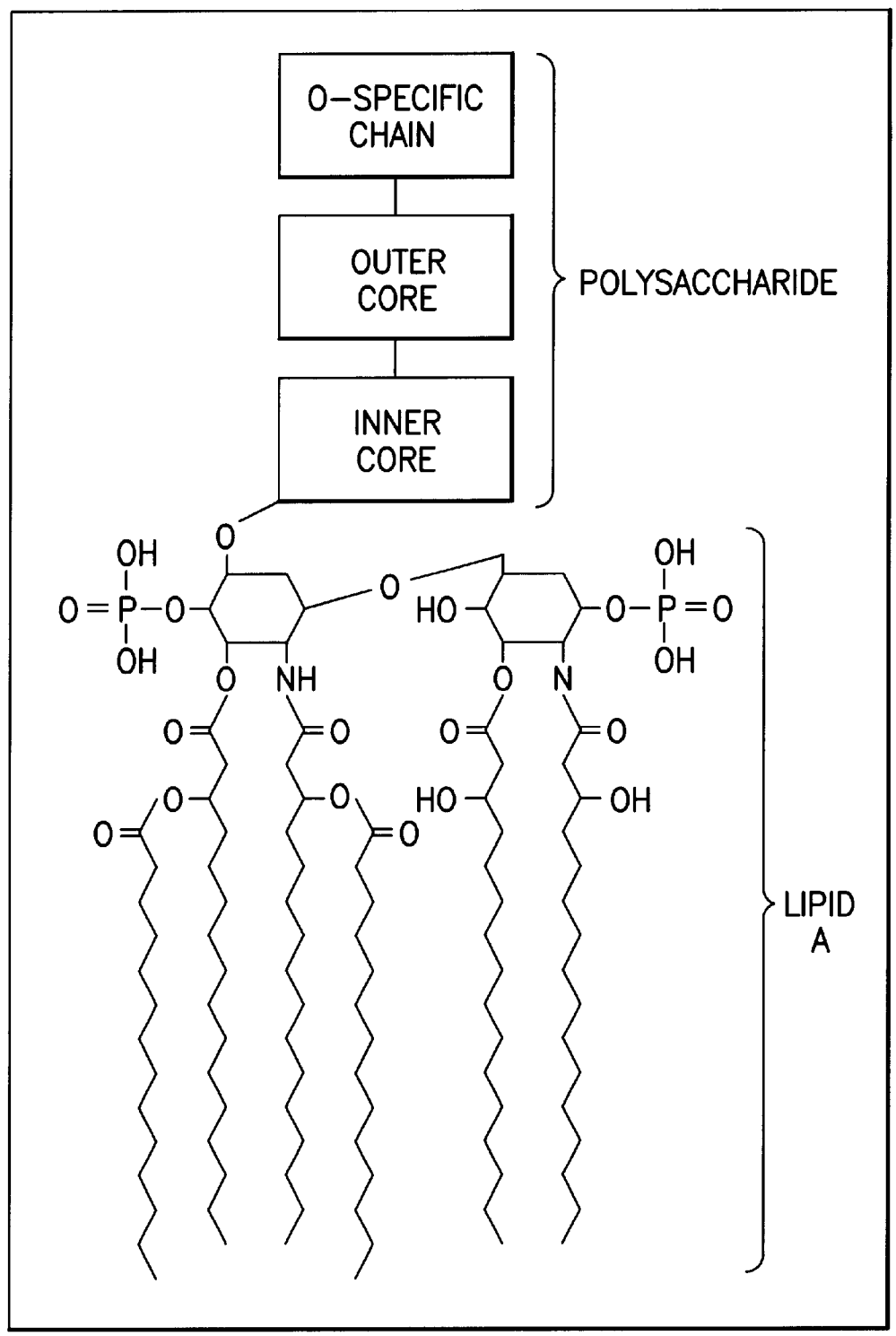
FIG. 1 is a diagram of an LPS molecule.

Prior to the present invention, LPS antagonists had proven to be poor adjuvants. An unexpected and surprising element of the present invention, therefore, is the finding that LPS preparations isolated from gram negative bacterial strains that contain at least one mutation in at least one of the hirB and msbB genes display both LPS antagonist and adjuvant activities. Accordingly, one embodiment of the present invention provides a novel adjuvant comprising an LPS antagonist. In particular, the present invention provides compositions comprising an LPS antagonist isolated from a gram negative bacterial strain that contains at least one mutation in at least one of the htrB and msbB genes. The invention also provides methods for enhancing the efficacy of a vaccine in a subject, comprising administering to the subject one or more antigens, against which an immune response is desired, with one or more LPS antagonists.

5.2 Definitions

For convenience, certain terms employed in the Specification, Examples, and appended Claims are collected here.

The term "adjuvant" refers to a compound that, when combined with a vaccine antigen, increases the immune response to the vaccine antigen over that induced by the vaccine antigen alone. An adjuvant may augment humoral immune responses or cell-mediated immune responses or both humoral and cell-mediated immune responses against vaccine antigens. The phrase "optimum adjuvant effect" refers to the lowest dose of an adjuvant required to induce or enhance an immune response against an antigen. The phrase "optimum adjuvant effect of the LPS antagonist" refers to the lowest dose of an LPS antagonist required to induce an immune response against an antigen.

The term "animal" refers to vertebrates, preferably mammals, and most preferably humans. Likewise, a "patient" or "subject" to be treated by the method of the invention can mean either a human or a non-human animal.

"Antigen" refers to any molecule that is capable of eliciting an immune reaction, whether a cell-mediated or humoral immune response, whether in the presence or absence of an adjuvant. An antigen can be any type of molecule, e.g., a peptide or protein, a nucleic acid, a carbohydrate, a lipid, and combinations thereof. A "vaccine antigen" is an antigen that can be used in a vaccine preparation. A "therapeutic antigen" is an antigen that can be used for therapeutic purposes.

The terms "biological activity", "bioactivity", "activity" and "biological function", when referring to a LPS or lipid A preparation, and which are used interchangeably herein, includes a biological response of a cell when contacted with LPS or lipid A, e.g., an increase in the production of a cytokine. A biological activity of an LPS or lipid A preparation also includes an effect of the LPS or lipid A on an organism, e.g, an increase in body temperature, i.e., fever; or toxicity, B-lymphocyte mitogenesis, macrophage activation, interferon production, tumor regression, peripheral vascular collapse ("endotoxic" shock), pulmonary hypertension, pulmonary edema, disseminated intravascular coagulopathy and pyrogenicity. An LPS bioactivity can also include the modulation of gene expression of LPS-responsive genes, e.g., IL-1, IL-6, RANTES, or TNF-α and the consequent serum levels of their gene products. Other biological activities of LPS include activation of cellular and humoral immunity, enhancement of the tumoricidal activity of macrophages and stimulation of the release of numerous inflammatory mediators such as tumor necrosis factor, arachidonic acid metabolites, complement components, reactive oxygen intermediates, nitric oxide, hydrolytic enzymes, thromboxane, prostacyclin, and platelet activating factor, chemoattractants, interleukin (IL)-8, leukotriene B4, and proteases. LPS bioactivity also includes phosphorylation of specific proteins including MAP kinases, e.g., MAPK1, MAPK4, and p38.

The terms "cells" and "host cells" and "recombinant host cells", which are used interchangeably herein, refer to cells which are capable of or have been transformed with a vector, typically an expression vector. A host cell can be prokaryotic or eukaryotic, including bacteria, insect, yeast and mammalian. The host cells used herein to prepare the LPS antagonist are preferably gram-negative bacteria. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "culture medium" is recognized in the art, and refers generally to any substance or preparation used for the cultivation of living cells. Exemplary bacterial media and culture conditions are described in Section 5.3.3.

The term "derived from", as used e.g., in the context of an antigen deriving from a bacterium or from a protein, refers to an antigen that can be obtained from the bacterium or the protein, and is intended to include fragments or portions of proteins.

The term "defective" as used herein, with regard to a gene or gene expression, means that the gene is not a wildtype gene and that the organism does not have a wildtype genotype and/or a wildtype phenotype. The defective gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wildtype gene expression.

The term "gram-negative bacteria" is recognized in the art, and refers generally to bacteria which do not retain Gram stain (i.e., the deposition of a colored complex between crystal violet and iodine). In an exemplary Gram stain, cells are first fixed to a slide by heat and stained with a basic dye (e.g., crystal violet), which is taken up by all bacteria (i.e., both gram-negative and gram-positive). The slides are then treated with an iodine-KI mixture to fix the stain, washed with acetone or alcohol, and finally counterstained with a paler dye of different color (e.g., safranin). Gram-positive organisms retain the initial violet stain, while gram-negative organisms are decolorized by the organic solvent and hence show the counterstain. Exemplary gram negative bacteria and cells lines are provided in Section 5.3.2 below. The term "mutant gram negative bacteria", as used herein, includes gram negative bacteria of the invention that have been mutated one or more times in one or more of the htrB and msbB genes, thereby producing LPS which is an LPS antagonist, non-pyrogenic, and an adjuvant.

An "immunogenic portion of a molecule" refers to a portion of the molecule that is capable of eliciting an immune reaction against the molecule in a subject.

The term "isolated" as applied to LPS or lipid A molecules, refers LPS or lipid A which has been isolated from other bacterial components, in particular from bacterial glycoproteins.

Figure 2:
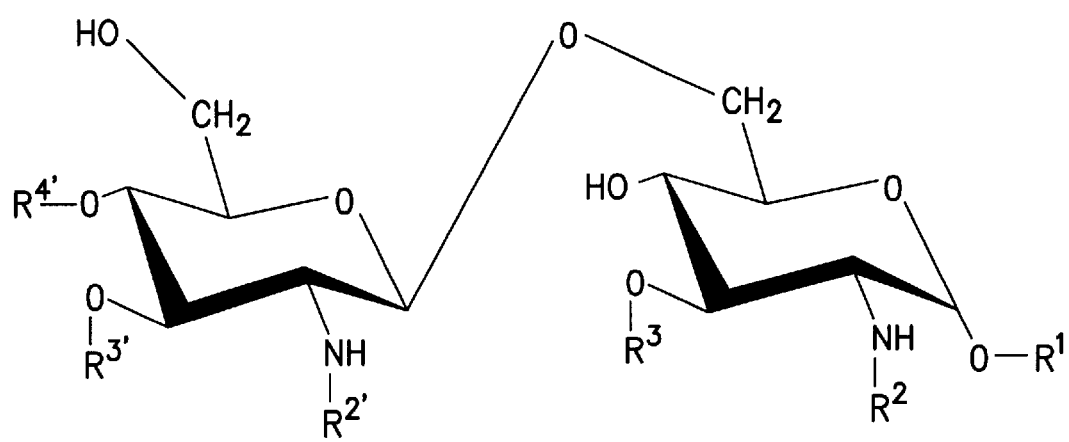
FIG. 2 is a diagram of a lipid A molecule.

The term "lipid A" refers to the hydrophobic portion of an LPS molecule that is linked to the inner core of the LPS molecule through an ester bond (FIGS. 1 and 2). Lipid A, as used herein includes both wildtype lipid A, analogs, derivatives and precursors thereof. The term is used herein as it is known in the art and includes the following structures: monosaccharides, e.g., the precursor of lipid A referred to as lipid X; disaccharide lipid A; hexa-acyl lipid A; penta-acyl lipid A; tetra-acyl lipid A, e.g., tetra-acyl precursor of lipid A, referred to as lipid IVA; monophosphoryl lipid A; diphosphoryl lipid A, such a lipid A from *Rhodobacter sphaeroides*; and penta-acyl lipid A.

The term "lipid A analog" refers to a lipid A molecule having essentially the same molecular structure as wildtype lipid A (FIG. 2) and having the same biological activity as wildtype lipid A. Lipid A analogs can be modified to be shortened or condensed, e.g., the carbon backbone may be shortened to a 5 carbon backbone. In another example, glucosamine residues are substituted with galactosamine residues. In yet another example, a synthetic analog contains a 2-deoxy-2-aminogluconate in place of the glucosamine-1-phosphate at the reducing end. In another illustrative embodiment, a synthetic analog bears a galacturonic acid moiety instead of a phosphate at position 4'. Lipid A analogs can be prepared from lipid A isolated from a bacterium, e.g., by first determining the structure of the isolated lipid A and synthesizing analogs thereof.

The term "lipid A derivative" is a lipid A analog that can be obtained from a wildtype lipid A by chemical derivation. For example, a lipid A derivative is a lipid A molecule that is obtained by deacylation of a wildtype lipid A molecule, e.g., by alkali treatment. Lipid A derivatives can be prepared from lipid A isolated from bacteria, as well as from synthetic lipid A molecules.

The term "LPS" or "lipopolyssaccharide" or "endotoxin", which are used interchangeably herein, are used as known in the art, and includes both wildtype LPS, analogs, and derivatives thereof. Thus, LPS is a molecule comprising an O-specific polysaccharide; a common core region; and a lipid component called lipid A (FIG. 1). The glycosidic units can be glycopyranosyl or glycofuranosyl, as well as their amino sugar derivatives. The residues may be homopolymers, random, or alternating or block copolymers thereof. The glycosidic units have free hydroxy groups, or acylated hydroxy groups. The glycosides can comprise up to 20 glycosidic units. Preferred, however, are those having less than 10, most preferred, those having 3 or less than 3 glycosidic units. Specific examples are those containing 1 or 10 glycosidic units in the glycoside residue. Among the possible glycopyranosyl structures are glucose, mannose, galactose, gulose, allose, altrose, idose, or talose. Among the furanosyl structures, the preferred ones are those derived from fructose, arabinose or xylose. Among preferred diglycosides are sucrose, cellobiose, maltose, lactose, trehalose, gentiobiose, and melibiose. Among the triglycosides, the preferred ones may be raffinose or gentianose. Among the amino derivatives are N-acetyl-D-galactosamine, N-acetyl-D-glucosamine, N-acetyl-D-mannosamine, -acetyineuraminic acid, D-glucosamine, lyxosylamine, D-galactosamine, and the like.

The term "LPS antagonist" refers to a compound, preferably an LPS or a lipid A molecule, or analog or derivative thereof, which inhibits or decreases at least one biological activity of wildtype LPS, such as the interaction between wildtype LPS and an LPS receptor on the surface of a cell, thereby decreasing the effect of the wildtype lipid A on the cell. An antagonist preferably inhibits one or more biological activities of a wildtype LPS by a factor of at least 10, preferably, at least about $10^2$, at least about $10^3$, at least about $10^4$, and most preferably by a factor of at least about $10^5$. For example, an antagonist preferably inhibits the binding of wildtype LPS to an LPS receptor by a factor of at least 10, preferably, at least about $10^2$, at least about $10^3$, at least about $10^4$, and most preferably by a factor of at least about $10^5$.

The term "LPS analog" refers to a molecule having essentially the same molecular structure as wildtype LPS (FIG. 1) and having the same biological activities as wildtype LPS. LPS analogs can be prepared from LPS isolated from a bacterium, e.g., by first determining the structure of the isolated LPS and synthesizing analogs thereof.

The term "LPS derivative" is an LPS analog that can be obtained from a wildtype LPS molecule by chemical derivation. Lipid A derivatives can be prepared from lipid A isolated from bacteria, as well as from synthetic lipid A molecules.

The term "LPS receptor" refers to a cell surface molecule to which a wildtype LPS molecule binds, either alone or together with another molecule, e.g., LPS binding protein (LBP), preferably with an affinity of at least about $10^{-5}$ M, preferably at least about $10^{-6}$ M, at least about $10^{-7}$ M, at least about $10^{-8}$ M, at least about $10^{-9}$ M, at least about $10^{-10}$ M, at least about $10^{-11}$ M, at least about $10^{-12}$ M, and even more preferably at least about $10^{-13}$ M. The affinity of a molecule for a receptor can be determined, e.g., by Scatchard analysis, well known in the art. LPS receptors are present on different types of cells including macrophages, neutrophils, erythrocytes, thrombocytes, endothelial cells, and hepatocytes. Examples of LPS receptors include CD 14 (see, e.g., U.S. Pat. No. 5,869,055), a macrophage/polymorphonuclear leukocyte differentiation antigen (Ferrero et al. (1990) J. Immunol. 145: 331 and Tobias et al. (1989) J. Biol. Chem. 264: 10867); a 70 kD scavenger receptor; the C 11 b/CD 18 complex; and moesin (Thome et al. (1999) Infect. Immun. 67:3215). Binding of LPS to its receptor may require the presence of another molecule, such as an LPS binding molecule, e.g., LBP (see, e.g., U.S. Pat. No. 5,837,810), which recognizes the lipid A region of LPS and forms complexes with both rough and smooth form LPS (Tobias et al., 1989, J. Biol. Chem. 264:10867–10871). Another LPS binding protein is bactericidal permeability-increasing factor, (BPI) (Tobias et al., 1988, J. Biol. Chem. 263:13479 13481; see also U.S. Pat. Nos. 5,856,438 and 5,827,816), having the amino acid sequence set forth in Gray et al. (1989) J. Biol. Chem. 264: 9505).

The term "mixture of LPS" or "mixture of lipid A", e.g., a heterologous mixture, refers to a composition comprising more than one LPS antagonist or derivative or analog thereof, whether synthetic or isolated from a microorganism. No specific amount, ratio, or number of different LPS antagonists is necessary to form a heterologous mixture. For example, such a mixture may contain two or more different types of lipid A molecules. In an illustrative embodiment, growth of an *E. coli* strain that is defective in htrB or in both htrB and msbB in permissive conditions (30° C.) yields a heterologous mixture of penta-acylated and some hexa-acylated forms of lipid A (Clementz et al., 1997, JBC 272:10353).

The term "lipid A precursor" or "lipid A precursor structure" refers precursor molecules or defective or mutant forms or fractions thereof, the wildtype form of which is required as a component in the synthesis of lipid A. Exemplary lipid A precursors are lipid X, tetraacyl-lipid A (LA4), pentaacyl-lipid A (LAS), and RsDPLA.

The term "modulation" as used herein refers to both upregulation (i.e., activation or stimulation (e.g., by agonizing or potentiating)) and downregulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

The term "mutated gene" refers to a form of a gene which is capable of altering the phenotype of a subject or host cell having the mutated gene relative to a subject or host cell which does not have the mutated gene.

The term "non-human animals" includes any animal that can be treated or used in testing the present invention, including mammals such as non-human primates, rodents, sheep, dogs, cows, pigs, chickens, as well as amphibians, reptiles, etc. Preferred non-human animals are selected from the primate family or rodent family (e.g., rat and mouse).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

"Permissive temperature" refers to a temperature at which, when a microorganism having a temperature sensitive mutation in a gene, is grown, the protein encoded by gene having a temperature sensitive mutation, is expressed in the microorganism. On the other hand, "non permissive temperature" is a temperature at which, when a microorganism having a temperature sensitive mutation in a gene, is grown, the protein encoded by the gene having a temperature sensitive mutation fails to accumulate in the microorganism, thereby resulting in a microorganism having a null phenotype, as if the gene was disrupted. A permissive temperature is a temperature that is below 33° C., whereas a non-permissive temperature is a temperature that is higher than 33° C.

The term "pharmaceutically acceptable" means a material that is not biologically or otherwise undesirable, i.e., the material may be administered to an individual along with the selected compound without causing any undesirable biological effects or interacting in a deleterious manner with any of the other compounds of the pharmaceutical composition in which it is contained.

The terms "protein", "polypeptide" and "peptide" are used interchangeably herein when referring to a gene product. The tern "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Likewise the term "recombinant nucleic acid" or "recombinant DNA" refers to a nucleic acid or DNA of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native polypeptide, or an amino acid sequence similar thereto which is generated by mutations including substitutions, insertions, and deletions (including truncation) of a naturally occurring form of the polypeptide.

The term "pyrogenic" or "pyrogenicity" refers to the ability of a compound to induce fever or a febrile response when administered to a subject. Such febrile responses are generally mediated by the host proinflammatory cytokines IL-1, IL-6 and/or TNF-α, the secretion of which is induced, e.g., by LPS. The phrase "pyrogenic activity" refers to any one of the activities associated with a pyrogenic response, including fever, toxic or endotoxic response in mammals, or the biosynthesis of pyrogenic cytokines, e.g., IL-7B, IL-6 or TNF-α, or other induced gene products. In a preferred embodiment and as demonstrated in the Examples below, pyrogenic activity can be measured by comparing the plasma levels in an animal of TNF-α in response to administration of a test substance and comparing those levels to the levels of TNF-α elicited by a control animal which does not receive the substance (i.e., receives a placebo). Other indicia of pyrogenic activity are well known in the art and include the increased synthesis of any of a number of acute phase reactants, many of which are proteins whose biosynthesis is induced by the proinflammatory cytokines. The phrase "non-pyrogenic" is used to describe a substance that does not induce fever or a febrile response, and does not exhibit pyrogenic activity at a detectable level.

A substance having "reduced pyrogenicity" or a "reduced pyrogenic derivative" refers to a substance (e.g., LPS or lipid A) having less pyrogenic activity than the counterpart wildtype substance, e.g., less than about 80% pyrogenic relative to the wildtype substance, preferably less than about 70% pyrogenic, more preferably less than about 60% pyrogenic, more preferably less than about 50°/" pyrogenic, more preferably less than about 40% pyrogenic, and even more preferably less than about 30% pyrogenic. In other terms, a substance having reduced pyrogenicity is at least about 20%, 30%, 40%, 50%, 60%, or 70% less pyrogenic than the corresponding wildtype substance as determined by any of the assays described herein or known in the art.

"Substantially reduced pyrogenicity" or "substantially reduced pyrogenic derivative" refers to a substance (e.g., LPS or lipid A), e.g., produced by a bacteria which has been genetically or epigenetically altered, that it has less than 20% pyrogenicity relative to the wildtype substance, preferably less than 10% pyrogenicity, preferably less than 1% pyrogenicity, preferably less than $10^{-1}$% pyrogenicity, preferably less than $10^{-2}$% pyrogenicity, preferably less than $10^{-3}$% pyrogenicity, preferably less than $10^{-4}$% pyrogenicity, preferably less than $10^{-5}$% pyrogenicity, and most preferably less than $10^{-6}$% pyrogenicity relative to the wildtype substance. In other terms, a substance that has substantially reduced pyrogenicity is at least about 90%, 99%, 10 fold, about $10^{-2}$ fold, about $10^{-3}$ fold, at least about $10^{-4}$ fold, at least about $10^{-5}$ fold, at least about $10^{-6}$ fold less pyrogenic relative to the corresponding wildtype substance as determined by any of the assays described herein or known in the art.

A "non-pyrogenic derivative" refers to a substance that has less than about $10^{-7}$ pyrogenicity of the wildtype substance, or in other terms, which is at least about 10' fold less pyrogenic than the corresponding wildtype substance.

The term "subject" is intended to include mammals, particularly humans, susceptible to diseases or conditions which can be treated with the present invention.

The term "substantially pure", with respect to an LPS or lipid A preparation of the invention, refers to LPS that is at least about 75%, preferably at least about 85%, more preferably at least about 90%, 95%, 98%, and most preferably at least about 99% pure, with respect to LPS or lipid A content of the preparation. The term "substantially pure" thus refers to an LPS or lipid A preparation of the present invention that contains less than about 20%, more preferably less than about 10%, 5%, 2%, and most preferably less than about 1%, of non LPS or lipid A components, e.g., organic components, such as phenol, nucleic acid, protein, polypeptide, amino acids, nucleotides, or other cellular, components. In a most preferred embodiment, an LPS or lipid A preparation is substantially pure if the LPS or lipid A preparation at a concentration of 100 µg/ml LPS or lipid A in milli-Q water does not show an absorption maxima at 260 nm or 280 nm. The absence of absorbance indicates that the sample contains less than 5 ng/ml of nucleic acid; and less than 50 ng/ml of protein.

As used herein, the term "transfection" means the introduction of a nucleic acid (e.g., via an expression vector) into a recipient cell by nucleic acid-mediated gene transfer. "Transformation", as used herein, refers to a process in which a cell's genotype is changed as a result of the cellular uptake of exogenous DNA or RNA. In an illustrative embodiment, a transformed cell is one that expresses a mutant form of one or more of the msbB and htrB genes. A transformed cell can also be one that expresses a nucleic acid which interferes with the expression of an msbB or htrB gene.

As used herein, the term "transgene" means a nucleic acid (e.g., a mutant msbB or htrB gene, or an antisense transcript thereto) which has been introduced into a cell. A transgene could be partly or entirely heterologous, i.e., foreign, to the transgenic animal or cell into which it is introduced, or, can be homologous to an endogenous gene of the organism or-cell into which it is introduced, but which is designed to be inserted, or is inserted, into the animal or cell's genome in such a way as to alter the genome of the cell into which it is inserted. A transgene can also be present in a cell in the form of an episome. A transgene can include one or more transcriptional regulatory sequences and any other nucleic acid sequences, such as 5' UTR sequences, 3' UTR sequences, or introns, that may be necessary for optimal expression of a selected nucleic acid.

The term "treating" a subject for a condition or disease, as used herein, is intended to encompass curing, as well as ameliorating at least one symptom of the condition or disease.

A "vaccine preparation" refers to a composition comprising one or more antigens for administration to a subject, to induce an immune response against the antigen in the subject.

The terms "vector," "cloning vector," or "replicative cloning vector," are interchangeable as used herein, and refer to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

The term "wildtype" refers to the most common phenotype or genotype in a natural population. The term "wildtype" may also refer to a phenotype or genotype arbitrarily designated as the standard for comparison. A wildtype organism has the phenotype or genotype most commonly found in nature as compared to a mutant organism.

The term "wildtppe lipid A" refers to lipid A having the molecular structure of a lipid A molecule isolated from a wildtype microorganism, i.e., a microorganism that has not been mutated in a laboratory by the hand of man. A preferred wildtype lipid A is a lipid A from an *E. coli* bacteria, e.g., W3110 (see Examples).

The term "wildtype LPS" refers to LPS having the molecular structure of an LPS molecule isolated from a wildtype microorganism, i.e., a microorganism that has not been mutated in a laboratory by the hand of man. A preferred wildtype LPS is an LPS from an *E. coli* bacteria, e.g., W3110, which can be purchased from Ribi ImmunoChem Research, Inc., Hamilton, Mont. (see Examples).

Additional terms are defined where appropriate below.

5.3 Adjuvant Preparations Comprising an LPS Antagonist

5.3.1 Non-Pyrogenic LPS and Lipid A

We have found that gram negative bacterial strains, which contain a conditional mutation (or mutations) that result in the accumulation of lipid A precursors, are capable of exclusively producing non-pyrogenic LPS (i.e., LPS that is $10^{-7}$-fold less toxic than wildtype LPS) under specific growth conditions in supplemented culture medium (see PCT International Publication Nos. WO 97/18837 and WO 99/15162, the teachings of which are incorporated herein by reference).

Examples of such conditional mutations that affect the biosynthesis of lipid A and result in the accumulation of non-pyrogenic LPS include, but are not restricted to, mutations in htrB, msbB, kdsA, kdsB, and kdtA (Rick, et al., 1977, supra; Rick and Osborne, 1977, supra; Raetz, et al., 1985, supra; Raetz, 1990, supra; Raetz, 1993, supra; Schnaitman and Klena, 1993, supra; Lee, et al., 1995, Infect. Immun., 63:818; Karow and Georgopoulos, 1991, Molec. Microbiol., 5:2285; Karow, et al., 1991, supra). These mutations could be introduced alone. Alternatively, any combination of mutations in the kdsA, kdsB, lpxB, kdtA, lpxC (synonym is envA), lpxD (synonyms are firA and ssc), ssc, lpxA, htrB, and the msbB genes (Rick, et al., 1977, supra; Rick and Osborne, 1977, supra; Raetz, et al., 1985, supra; Raetz, 1990, supra; Raetz, 1993, supra; Schnaitman and Klena, 1993, supra; Lee, et al., 1995, supra; Karow and Georgopoulos, 1991, supra; Karow, et al., 1991, supra; Karow and Georgopoulos, 1991, supra), which may affect the biosynthesis of lipid A and result in the synthesis of non-pyrogenic lipid A structures, could be used.

5.3.2 Preparation of Mutants that Produce an LPS Antagonist

A mutation in a gene, e.g., of a gram negative bacterium, such as a mutation in a hirb and msbB gene, can be introduced using any well-known genetic technique. These include but are not restricted to non-specific mutagenesis, using chemical agents such as N-methyl-N'-nitro N-nitrosoguanidine, acridine orange, ethidium bromide, or non-lethal exposure to ultraviolet light (Miller (Ed.), 1991, In: A Short Course in Bacterial Genetics, Cold Spring Harbor Press, Cold Spring Harbor, N.Y.). Alternatively, the mutations can be introduced using Tn10 mutagenesis, bacteriophage-mediated transduction, lambda phage-mediated allelic exchange, or conjugational transfer, or site directed mutagenesis using recombinant DNA techniques (Miller (Ed.), 1991, supra; Hone, et al., 1987, J. Infect. Dis., 156:167; Noriega, et al, 1994, Infect. Immun., 62:5168; Hone, et al., 1991, Vaccine, 9:810; Chatfield, et al., 1992, Vaccine, 10:53; Pickard, et al., 1994, Infect. Immun., 62:3984; Odegaard, et al., 1997, J. Biol. Chem., 272:19688; Lee, et al., 1995, J. Biol. Chem., 270:27151; Garrett, et al., 1998, J. Biol. Chem., 273:12457). Any method for introducing mutations may be used and the mutations can be introduced in conjunction with one or more additional mutations, such as those described in PCT International Publication Nos. WO 97/18837 and WO 99/15162, the teachings of which are incorporated herein by reference.

The mutations can be either constitutively expressed or under the control of inducible promoters, such as the temperature sensitive heat shock family of promoters (Neidhardt, et al., supra), or the anaerobically-induced nirB promoter (Harborne, et al., 1992, Mol. Micro., 6:2805) or repressible promoters, such as uapA (Gorfinkiel, et al., 1993, J. Biol. Chem., 268:23376) or gcv (Stauffer, et al., 1994, J. Bact, 176:6159). Selection of the appropriate promoter will depend on the host bacterial strain and will be obvious to those skilled in the art.

5.3.3 Bacterial Strains

Any gram negative bacterial strain can be used as a source of LPS antagonist in the practice of the present invention. Examples of gram-negative bacteria include, but are not limited to, Escherichia spp., Shigella spp., Salmonella spp., Campylobacter spp., Neisseria spp., Haemophilus spp., Aeromonas spp., Francisella spp., Yersinia spp., Klebsiella spp., Bordetella spp., Legionella spp., Corynebacterium spp., Citrobacter spp., Chlamydia spp., Brucella spp., Pseudomonas spp., Helicobacter spp. and Vibrio spp.

The particular Escherichia strain used in the practice of the present invention is not critical. Examples of Escherichia strains which can be used include *Escherichia coli* (*E. coli*) strains DH5a, HB 101, HS-4, 4608-58, 1-184-68, 53638-C-17, 13-80, and 6-81 (Sambrook, et al., (Eds.), 1993, In: Molecular Cloning, Cold Spring Harbor Press, Cold Spring Harbor, N.Y.); Grant, et al., 1990, Proc. Natl. Acad. Sci., USA, 87:4645; Sansonetti, et al., 1982, Ann. Microbiol. (Inst. Pasteur), 132A:351), enterotoxigenic *E. coli* (Evans, et al., 1975, Infect. Immun., 12:656), enteropathogenic *E. coli* (Donnenberg, et al., 1994, J. Infect. Dis., 169:831) and enterohemorrhagic *E. coli* (McKee and O'Brien, 1995, Infect. Immun., 63:2070).

The particular Shigella strain used in the practice of the present invention is not critical. Examples of Shigella strains which can be used include *S. flexneri* (ATCC No. 29903), *S. sonnei* (ATCC No. 29930), and *S dysenteriae* (ATCC No. 13313).

The particular Campylobacter strain used in the practice of the present invention is not critical. Examples of Campylobacter strains which can be used include but are not limited to *C. jejuni* (ATCC Nos. 43436, 43437, 43438), *C. hyointestinalis* (ATCC No. 35217), *C. fetus* (ATCC No. 19438) *C. fecalis* (ATCC No. 33709) *C. doylei* (ATCC No. 49349) and *C. coli* (ATCC Nos. 33559, 43133).

The particular Yersinia strain used in the practice of the present invention is not critical. Examples of Yersinia strains which can be used include *Y. enzerocolitica* (ATCC No. 9610) or *Y. pestis* (ATCC No. 19428), *Y. enterocolitica* Ye03-R2 (al-Hendy, et al., 1992, Infect. Immun., 60:870) and a *Y. enterocolitica* aroA mutant (O'Gaora, et al., 1990, Micro. Path., 9:105).

The particular Klebsiella strain used in the practice of the present invention is not critical. Examples of Klebsiella strains which can be used include *K. pneumoniae* (ATCC No. 13884).

The particular Bordetella strain used in the practice of the present invention is not critical. Examples of Bordetella strains which can be used include *B. pertussis* and *B. bronchiseptica* (ATCC No. 19395).

The particular Neisseria strain used in the practice of the present invention is not critical. Examples of Neisseria strains which can be used include *N. meningitidis* (ATCC No. 13077) *N. gonorrhoea* (ATCC No. 19424) and an *N. gonorrhoea* MS 11 aro mutant (Chamberlain, et al., 1993, Micro. Path., 15:51–63).

The particular Aeromonas strain used in the practice of the present invention is not critical. Examples of Aeromonas strains which can be used include *A. salminocida* (ATCC No. 33658), *A. schuberii* (ATCC No. 43700), *A. hydrophila* and *A. eucrenophila* (ATCC No. 23309).

The particular Francisella strain used in the practice of the present invention is not critical. Examples of Francisella strains which can be used include *F. tularensis* (ATCC No. 15482).

The particular Corynebacterium strain used in the practice of the present invention is not critical. Examples of Corynebacterium strains which can be used include *C. pseudotuberculosis* (ATCC No. 19410).

The particular Citrobacter strain used in the practice of the present invention is not critical. Examples of Citrobacter strains which can be used include *C. freundii* (ATCC No. 8090). The particular Chlamydia strain used in the practice of the present invention is not critical. Examples of Chlamydia strains which can be used include *C. pneumoniae* (ATCC No. VR1310).

The particular Haemophilus strain used in the practice of the present invention is not critical. Examples of Haemophilus strains which can be used include *H. influenzae* (Lee, et al., 1995, supra) and *H. somnus* (ATCC No. 43625).

The particular Brucella strain used in the practice of the present invention is not critical. Examples of Brucelia strains which can be used include *B. abortus* (ATCC No. 23448).

The particular Legionella strain used in the practice of the present invention is not critical. Examples of Legionella strains which can be used include *L. pneumophila* (ATCC No. 33156), and a *L. pneumophila* mip mutant (Ott, 1994, FEMS Micro. Rev., 14:161).

The particular Pseudomonas strain used in the practice of the present invention is not critical. Examples of Pseudomonas strains which can be used include *P. aeruginosa* (ATCC No. 23267).

The particular Helicobacter strain used in the practice of the present invention is not critical. Examples of Helicobacter strains which can be used include *H. pylori* (ATCC No. 43504) and *H. mustelae* (ATCC No. 43772).

The particular :Salmonella strain used in the practice of the present invention is not critical. Examples of Salmonella strains which can be used include *S. typhi* (ATCC No. 7251), *S. typhimurium* (ATCC No. 13311), *S galinarum* (ATCC No. 9184), *S. enteridilis* (ATCC No. 4931) and *S. typhimurium* (ATCC No. 6994), an *S. typhi* aroC, aroD mutants (Hone, 1991, et al., Vacc., 9:810–816) and an *S. typhimurium* aroA mutant (Mastroeni, et al., 1992, Micro. Pathol., 13:477491).

The particular Vibrio strain used in the practice of the present invention is not critical. Examples of Vibrio strains which can be used include *Vibrio cholerae* (ATCC No. 14035), *Vibrio cincinnatiensis* (ATCC No. 35912), a *V. cholerae* RSI virulence mutant (Taylor, et al., 1994, J. Infect. Dis., 170:1518–1523) and a *V. cholerae* ctxA, ace, zot, cep mutant (Waldor, et al., 1994, J. Infect. Dis., 170:278–283). Useful non-pyrogenic bacterial strains and their uses are disclosed in PCT International Publication Nos. WO 97/18837 and WO 99/15162, the teachings of which are incorporated herein by reference.

5.3.4 Bacterial Culture

The specific culture conditions for the growth of the mutant gram negative bacterial strains for the preparation of an adjuvant comprising an LPS antagonist are not critical to the present invention. For illustrative purposes, bacteria can be grown in any standard liquid medium suitable for bacterial growth, such a LB medium (Difco, Detroit Mich.), Nutrient broth (Difco), Tryptic Soy broth (Difco), or M9 minimal broth (Difco), using conventional culture techniques that are appropriate for the bacterial strain being grown (Miller, 1991, supra). As an alternative the bacteria can be cultured on solid media such as L-agar (Difco), Nutrient agar (Difco), Tryptic Soy agar (Difco), or M9 minimal agar (Difco).

The temperature at which the bacterial strains are cultured is not crucial to the present invention. However, individual bacterial strains may produce a non-pyrogenic LPS antagonist at one temperature and at other temperatures produce a pyrogenic LPS antagonist. For example, *E. coli* htrB msbB double mutants produce LPS that retains modest pyrogenic activity at 30° C., but at temperatures above 33° C. and below 44° C., this strain produces a non-pyrogenic LPS antagonist (Hone, et al., 1998, supra).

A straight forward approach to identifying the optimal temperature for the culture of a particular bacterial strain is to grow the bacteria over a range of culture temperatures, isolate LPS from each culture (as described herein below) and measure the LPS antagonist activity of the LPS produced (as described in Hone, et al., 1998, supra). In this manner, culture temperatures can be identified that result in the production of non-pyrogenic or substantially lowered pyrogenic LPS antagonist by the bacterial strains.

Normally, exclusive expression of lipid A precursors is toxic to the bacterium. Thus, when these mutants are grown in non-permissive conditions, whereby lipid A precursors accumulate, the bacteria usually only undergo a single division before ceasing to grow. For example, in certain lipid A-defective mutants, expression of lipid IVa (a tetraacyl precursor of lipid A) can only reach levels of 30%–50% of the total LPS before growth of the strain ceases (Rick and Osborn, 1977, supra; Raetz, 1993, supra).

However, surprisingly, growth of the conditional mutants that produce lipid A precursors in non-permissive conditions, i.e., at 35° C. to 44° C., in the presence of quaternary cationic compounds, suppresses the conditional-lethal effect of these mutations and allows the accumulation of non-pyrogenic LPS/lipid A precursors (see below). Thus, under these culture conditions the bacteria continue to grow and accumulate substantially pure (>99%) non pyrogenic LPS.

The culture of htrB mutants at temperatures above 33° C. can be enhanced by the presence of quaternary cationic compounds, which suppress the temperature-sensitive effect of this mutation (Karrow and Georgopoulos, 1992, J. Bacteriol., 174:702; Powell and Hone, 1995, U.S. Pat. No. 5,877,159). The particular quaternary cationic compound used is not critical to the practice of the present invention. Examples include tetraacyltetramethylammonium bromide (herein TTAB; Sigma, St Louis Mo., USA), polylysine (Sigma), polymyxin (Sigma), ethanolamine (Sigma) dimethyldictadecylammonium bromide (DDAB from ICN, Costa Mesa, Calif., USA), 1,2, diacyl-3-trimethylammonium-propane (TAP; Avanti Polar Lipids Inc, AL, USA), 2,-dioleyloxy-N-[2(perminecarboxamindo)-ethyl]-N,N-dimethyl-1-propanammoniumtrifluoroacetate (DOSPA; GibcoBRL, Gaithersburg, Md., USA), and N-[1-2,3 dioleyloxy)propyl]-N,N,N-trimethylammonium chloride (DOTMA; GibcoBRL) (Powell and Hone, 1995, supra).

The concentration of the quaternary cationic compound in the medium is not critical to the practice of the present invention but it is usually a concentration that is sublethal to the bacterial strain, ranging from 0.01 $\mu$g/ml to 100 $\mu$g/ml. The concentration of quaternary cationic compound selected will depend on the genotype of the bacterial host and can be identified by growing the mutant organism at non-permissive temperatures in the presence of quaternary cationic compound at concentrations in this range.

The optical density at 600 nm at which the bacteria are harvested is not critical, and can range from 0.1 to 5.0 and will be dependent on the specific strain, media and culture conditions employed.

The method used to extract LPS is not critical to the practice of the present invention and can be any one of the well-known methods for LPS extraction (Garrett, et al., 1997, J. Biol. Chem., 272:21855; Garrett, et al., 1998, J. Biol. Chem., 273:12457; Clementz, et al., 1996, supra; Clementz, et al., 1997, supra; Somerville, et al., 1996, supra; Lee, et al., 1995, supra; Sunshine, et al., 1997, supra; Galanos, et al., 1969, Eur. J. Biochem., 9:245; Westphal, et al., 1952, Naturforsch, 7b:155; Westphal and Jann, 1965, In: Methods in Carbohydrate Chemistry, Whistler (Ed.), 5:83).

For example, the LPS antagonist can be extracted using the well-known hot phenol-water extraction procedure (Galanos, et al., 1969, supra; Westphal, et al., 1952, supra; Westphal and Jann, 1965, supra). After culturing the bacteria as described above, the bacteria are harvested by centrifugation (4,500×g for 15 minutes) and washed once in endotoxin-free irrigation saline (0.85% w/v; Baxter). The weight of the bacterial pellets is determined and the bacteria are resuspended in endotoxin-free saline (Baxter) at a final density of 2% w/v and heated to 70° C. An equal volume of pre-warmed $H_2O$-equilibrate phenol (70° C.) is added to each of the bacterial suspensions and mixed for 15 minutes at 70° C. The mixtures are cooled to 25° C. and centrifuged at 18,000×g for 15 minutes. Following centrifugation, the aqueous phases are removed, placed into dialysis tubing (SpectraPor) and dialyzed against running milli-Q H20 (Millipore) for 24 hours. The retentates are then placed into fresh 50 ml polypropylene tubes and treated first with RNaseA (100 [$\mu$g/ml; Sigma) at 37° C. for 1 hour, then with DNaseI (50 $\mu$g/ml and 5 mM $MgCl_2$; Sigma) at 37° C. for 2 hours, and finally with Pronase (250 ;g/ml; Sigma) at 37° C. for 4 hours. EDTA is then added to a final concentration of 5 mM and the hot-water phenol extraction procedure described above is repeated. Following dialysis against running milli-Q $H_2O$ (Millipore) for a further 48 hours, residual particulate material is removed by centrifugation at 20,000×g for 1 hour. Ultrapure LPS is subsequently separated from the resultant supernatants by centrifugation at 100,000×g for 1 hour. The resultant high-speed centrifugation supernatants are discarded and the 100,000×g LPS pellets are lyophilized, as described in Hone, et al., 1995, supra. The lyophilates are weighed and resuspended in endotoxin-free PBS (<0.001 EU/ml; Lifetechnologies) at a concentration of 1–10 mg/ml and stored at −20° C.

5.3.6 Purity Determination of an LPS Antagonist

The purity of the LPS antagonist preparation (e.g., 10 $\mu$g) can be assessed by SDS-polyacrylamide gel electrophoresis and silver staining procedures, using commercially available reagents (Bio-Rad, Hercules Calif.). In addition, the purity of the LPS antagonist preparations can be evaluated by UV spectrophotometry (Shimadzu UV-1201S UV-VIS Spectrophotometer), wherein no significant absorption maxima should be detected in LPS preparations suspended in milli-Q HZO at 100 $\mu$g/ml. The absence of absorption maxima indicates that the preparation does not contain substantial amounts of phenol, nucleic acids or polypeptides, i.e., the preparation contains less than 5 ng/ml of nucleic acids and less than 50 ng/ml of protein. In each instance, 10-fold serial dilutions of E. coli genomic DNA (50–0.5 ng/100 $\mu$g LPS) and lysosyme (500–5 ng/100 $\mu$g LPS; Sigma) mixed with the LPS antagonist preparations can be used as internal controls.

5.3.7 Purification of the Lipid A Fraction from an LPS Antagonist

While one embodiment of the current invention provides an adjuvant comprised of LPS antagonist isolated from mutant gram negative bacterial strains using the above extraction procedure, in another embodiment the adjuvant can be prepared by isolating the lipid A fraction of the LPS preparation.

Procedures for isolating the lipid A fraction from LPS are well known in the art (see, e.g., Garrett, et al., 1997, supra; Garrett, et al., 1998, supra; Clementz, et al., 1996, supra; Clementz, et al., 1997, supra). For illustrative purposes, the lipid A fraction can be isolated from an LPS antagonist preparation by mild acid hydrolysis in 1% SDS at pH 4.5. The lipid A fraction can then be isolated by conventional DEAE-cellulose column chromatography techniques (Garrett, et al., 1997, supra; Garrett, et al., 1998, supra; Clementz, et al., 1996, supra; Clementz, et al., 1997, supra).

Lipid A can be analyzed by a number of techniques, including conventional thin layer chromatography (TLC) procedures, using silica gel-20 TLC plates (Garrett, et al., 1997, supra; Garrett, et al., 1998, supra; Clementz, et al., 1996, supra; Clementz, et al., 1997, supra). Wild type lipid A, LA4 and LAS can be used as standards (Clementz, et al., 1996, supra; Clementz, et al., 1997, supra). In addition, the molecular mass the lipid A can be determined by matrix-assisted laser desorption-ionization time-of-flight (MALDI-TOF) and electronspray analysis (Somerville, et al., 1996, supra; Lee, et al., 1995, supra; Sunshine, et al., 1997, supra).

The latter analysis combined with the analysis of the pyrogenic activity of each species will determine the purity, structure and biological activity of the lipid A fraction and can provide a template for the development of synthetic lipid A partial structures that mimic the adjuvant activity of said LPS antagonist using procedures well known in the art (Galanos, et al., 1984, Eur. J. Biochem., 140:221; Manthey, et al., 1993, Infect. Immun., 61:3518; Homma, et al., 1989, Drugs Future, 14:645; Steutz, et al., 1990, In: Endotoxin research series, Nowotny, et al., (Eds.), 1:129; Van Dervort, et al., 1992, J. Immunol., 149:359; Perera, et al., 1993, Infect. Immun., 61:2015; Kotani, et al., 1985, Infect. Immun., 49:225; Kotani, et al., 1986, supra; Fagan, et al., 1994, J. Immunol., 153:5230; Wang, et al., 1991, supra; Christ, et al., 1994, Am. Chem. Soc., 116:3637; Rose, et al., 1995, Infect. Immun., 63:833; Lam, et al., 1991, supra; Marcher, 1987, Carbohydrate Res., 162:79).

5.3.8 Determination of the Molecular Structure of an LPS or Lipid A Molecule Various methods well known in the art can be used to determine the molecular structure of an LPS or lipid A molecule isolated and purified from bacteria. Exemplary methods are described, e.g, in U.S. Pat. No. 5,648,343, in which the molecular structure of lipid A from Phizobium leguminosarum was determined. In particular, this patent describes methods for determining the glycosyl composition, fatty acid composition, glycosyl linkage analysis, and phosphate content of lipid A preparations. Such methods may involve NMR Spectroscopy and high resolution mass spectrometry, e.g., fast atom bombardment mass spectrometry (FAB-MS).

5.3.9 Synthetic LPS and Lipid A

Synthetic LPS and lipid A molecules with strong LPS antagonist properties and of reduced or absent pyrogenicity may be synthesized by a variety of organic chemistry synthetic techniques. In one embodiment of the present invention, the synthetic lipid A and LPS molecules are modeled after LPS molecules of reduced or absent pyrogenicity which occur in nature and molecules with strong LPS antagonist activities which occur in nature. Thus, the invention provides methods for preparing synthetic LPS and lipid A molecules that are identical to, analogs or derivatives of, naturally occurring LPS or lipid A molecules. As described in the previous section, methods for determining the structure of an LPS or lipid A molecule are well known in the art and can be used to first determine the structure of an LPS or lipid A molecule of interest, prior to synthesizing the same or similar LPS or lipid A molecules using organic chemistry methods.

For an overview of the synthesis of LPS and lipid A structures, see, e.g., Raetz, 1993, J. Bacteriology 175:5745–5753. (See also U.S. Pat. Nos. 5,593,969 and 5,191,072).

As set forth above, LPS is a complex polymer in four pats (see FIG. 1). Outermost is a carbohydrate chain variable length (called the O-antigen) which is attached to a core polysaccharide. The core polysaccharide is divided into the outer core and the backbone. These two structures vary between bacteria. Finally the backbone is attached to a glycolipid called lipid A. The link between lipid A and the rest of the molecule is usually via a number of 3-deoxy-D-manno-octulosonic acid (KDO) molecules. The presence of KDO is often used as a marker for LPS (or outer membrane) even though it is not present in all bacterial LPS. The phosphate and 3-deoxy-D-mannooctulosomic acid (KDO) molecules (the presence of KDO is often used as a marker for lipopolysaccharide) are also substituted. Unsaturated and cyclopropane fatty acids which are common in other lipid types are absent from LPS.

Lipid A is composed of a disaccharide of glucosamines. The amino groups are substituted with 3-hydroxymristate while hydroxyl groups contain saturated (12–16 carbon) acids and 3-myristoxymyristate. LPS and lipid A may be obtained from commercial sources, e.g., from Sigma. However, by way of example, but not by way of limitation, LPS may be synthesized as follows: hydroxy acids and disaccharides are condensed followed by addition of saturated fatty acids. The hydroxy fatty acids may come from acetyl CoA whereas CMP-KDO may serve as the source of the second additional units. After the addition of saturated fatty acids, sugars are added from nucleotide diphosphate derivatives.

The O-antigen is may be synthesized in three stages. For example, but not by way of limitation, the oligosaccharide units are transferred from nucleotide diphosphate carriers to a galactose attached to another lipid carrier. The oligosaccharide units are then polymerized and lipid carriers are released in the process. Finally the complete O-antigen is transferred to the R core with the release of an isoprenoid carrier.

The polysaccharide unit may also be synthesized with donor saccharide moieties and acceptor moieties which are commercially available and/or may be synthesized through organic synthesis applying techniques known in the art. Activated saccharides generally consist of uridine or guanosine diphosphate and cytidine monophosphate derivatives of the saccharides in which the nucleoside mono and diphosphate serves as a leaving group. Thus, the activated saccharide may be a saccharide-UDP, a saccharide-GDP, or a saccharide-CMP. Nucleoside monophosphates are commercially available, may be prepared from known sources such as digested yeast RNA (see e.g., Leucks et al,. 1979, J. Am. Soc. 101:5829), or routinely prepared using known chemical synthetic techniques (see e.g., Heidlas et al., 1992, Ace. Chem. Res. 25:307; Kochetkov et al., 1973, Adv. Carbohydr. Chem. Biochem. 28:307). These nucleoside monophosphates may then be routinely transformed into nucleoside diphosphates by kinase treatment. For review, see Wong et al., 1994, Enzymes in Synthetic Organic Chemistry, Pergamon Press, Volume 12, pp. 256–264.

Glycosyltransferase enzymes for synthesizing the compositions of the invention can be obtained commercially or may be derived from biological fluids, tissue or cell cultures. Such biological sources include, but are not limited to, pig serum and bovine milk. Glycosyltransferases that catalyze specific glycosidic linkages may routinely be isolated and prepared as described in International Patent Publication No. WO 93/13198 (published Jul. 8, 1993). Alternatively, the glycosyltransferases can be produced through recombinant or synthetic techniques known in the art (For review, see Wong et al., 1994, Enzymes in Synthetic Organic Chemistry, Pergamon Press, Volume 12, pp. 275–279).

The compositions of the invention are preferably synthesized using enzymatic processes (see e.g., U.S. Pat. No. 5,189,674, and International Patent Publication No. 91/16449, published Oct. 31, 1991). Briefly, a glycosyltransferase is contacted with an appropriate.

The compositions of the invention are preferably synthesized using enzymatic processes (see e.g., U.S. patent application Ser. No. 5,189,674, and International Patent Publication No. 91/15449, published Oct. 31, 1991). Briefly, a glycosyltransferase is contacted with an appropriate activated saccharide and an appropriate acceptor molecule under conditions effective to transfer and covalently bond the saccharide to the acceptor molecule. Conditions of time, temperature, and pH appropriate and optimal for a particular saccharide unit transfer can be determined through routine testing, generally, physiological conditions will be acceptable. Certain co reagents may also be desirable; for example, it may be more effective to contact the glycosyltransferase with the activated sugar and the acceptor molecule in the presence of a divalent cation.

Optionally, an apparatus as described by U.S. Pat. No. 5,288,637, is used to prepare such compositions.

While glycosyltransferases are highly stereospecific and substrate-specific, minor chemical modifications are tolerated on both the donor and acceptor components. Accordingly, the oligosaccharide components of the invention may be synthesized using acceptor and/or donor components that have been modified so as not to interfere with enzymatic formation of the desired glycosidic linkage. The ability of such a modification not to interfere with the desired glycosidic linkage may routinely be determined using techniques and bioassays known in the art, such as, for example, labeling the carbohydrate moiety of the activated sugar donor, contacting the acceptor and donor moieties with the glycosyltransferase specific for forming the glycosidic linkage between the donor and acceptor moieties, and determining whether the label is incorporated into the molecule containing the acceptor moiety.

5.3.10 LPS and Lipid A Analogs and Derivatives

Also included within the scope of the present invention are LPS and lipid A molecules which are differentially modified during or after synthesis, or after isolation from bacteria, e.g., to reduce their pyrogenicity. In specific embodiments, the LPS and lipid A molecules are treated by alkaline hydrolysis or acyloxyacyl hydrolase. Any of numerous chemical modifications may be carried out by known techniques, such as acylation, deacylation, formylation, oxidation, reduction, etc.

It is also within the scope of this invention, to synthesize analogs of lipid a having one or mere acyloxyacyl groups removed. Lipid A, either chemically synthesized or isolated from a gram negative microorganism may be treated with acyloxyacyl hydrolase in order to achieve or enhance the non-pyrogenic properties of the preparation. Acyloxyacyl hydrolase hydrolyzes the ester bonds between non-hydroxylated fatty acids and the 3-hydroxy functions of 3-hydroxy fatty acids bound in ester or amide linkages to glucosamine disaccharide of lipid A.

It is further within the scope of this invention, to synthesize analogs of lipid A and LPS having one or more non-hydroxylated fatty acids removed. Lipid A or LPS either chemically synthesized or isolated from a gram negative microorganism may be deacylated in order to achieve or enhance the substantially reduced or absent pyrogenicity of the preparation.

5.3.11 Measurement of Biological Activity of an LPS Antagonist

Whether an LPS or lipid A preparation is an LPS antagonist and is devoid of pyrogenic activity can be assessed using any of a number of methods.

Various tests can be used to demonstrate that a compound is an LPS antagonist (see Examples section herein). For example, various amounts of the test compound can be incubated with a cell having LPS receptors and wildtype LPS, e.g., LPS from $E.\ coli$ W3110, in conditions under which, but for the presence of the test compound, the wildtype LPS binds to the LPS receptor and induces LPS biological activities. One or more biological activities of LPS are then monitored and compared to those obtained when cells and wildtype LPS are incubated in the absence of the test compound. Optionally, the test comprises an LPS binding protein. The presence of a decrease in one or more biological activities of wildtype LPS in the presence of the compound relative to the absence of the compound indicates that the test compound is an LPS antagonist. A similar test in which the effect of a test compound on at least one biological activity of LPS is determined can also be performed in vivo, e.g., in a test animal such as a mouse. For example, the blood level of TNF can be measured in mice to which wildtype LPS and one of several doses of a test compound is administered (as described, e.g., in U.S. Pat. No. 5,158,939).

Another test that can be used to determine whether a compound is an LPS antagonist comprises contacting an LPS receptor, present on a cell surface or in a soluble form, with wildtype LPS in the presence of various amounts of the test compound. The extent of binding of the wildtype LPS to the soluble receptor can be detected, e.g., by labeling the LPS and/or the receptor, and by measuring the amount of label bound to either the receptor, the LPS, or both. LPS can be labeled with $^3$H-acetate as described, e.g., in Munford et al. (1992) J. Immunol. Methods 148: 115 and can have a specific activity of at least 106 dpm/$\mu$g.

In a specific embodiment, for determining the LPS antagonistic activity of a test compound, the assay comprises a cell which has been modified, e.g, transfected, to express an LPS receptor, such as CD14. CD14 cDNA can be cloned in the expression vector, e.g., pRc/RSV (Invitrogen, San Diego, Calif.) as previously described by Lee et al., J. Exp. Med., 175:1697 1705 (1992). CD14 expression can be detected by flow microfluorometry using FITC-MY-4 (Coulter, Hialeah, Fla.) and cells expressing CD 14 were selected by fluorescence-activated cell sorting with FITC-MY-4.

The pyrogenic activity of an LPS or lipid A can be determined by measuring, e.g., the production of pyrogenic cytokines by cells contacted with the LPS or lipid A preparation, e.g., by ELISA, as further described herein.

In another illustrative embodiment, a peripheral blood mononuclear cell (PBMC) activation assay can be used to assess the pyrogenic and LPS antagonist activities of an LPS antagonist preparation. These methods are well documented (Theofan, et al., 1994, J. Immunol., 152:3623; Fagan, et al., 1994, J. Immunol., 153:5230; Verhasselt, et al., 1997, J. Immunol., 158:2919; Colotta, et al., 1992, J. Immunol., 148:760; Mackensen, et al., 1992, Eur. Cyto. Net., 3:571; Eggesbo, et al., 1994, Cytokine, 6:521; Hone, et al., 1998, supra). Briefly, human PBMCs are isolated from whole blood and suspended at a density of $5 \times 10^5$ per ml in complete medium (CM; RPMI containing 10 $\mu$g/ml of pyruvate and glutamine, 100 $\mu$g/ml of penicillin and streptomycin, and 10% (v/v) endotoxin-free human AB serum (Life Technologies)). The PBMCs are then placed into 48 well flat-bottom culture plates (Costar), and stimulated with an LPS antagonist preparation (to measure the pyrogenic activity) or mixtures of an LPS antagonist and Re LPS (Sigma) to measure LPS antagonist activity, as described (Kovach, et al., 1990, supra; Golenbock, et al., 1991, supra; Golenbock, et al., 1988, supra; Kitchens, et al., 1992, supra; Kitchens and Munford, 1995, supra; Munford and Hunter, 1992, supra; Rietschel, et al., 1994, supra; Ulmer, et al., 1992, supra; Ulmer, et al., 1992, supra; Wang, et al., 1990, supra; Wang, et al., 1991, supra; Qureshi, et al., 1991, supra; Qureshi, et al., 1991, supra; Zuckerman and Qureshi, 1992; Hone, et al., 1998, supra). In positive control wells the PBMCs are stimulated with comparable doses of E. coli Re LPS (Sigma) in place of the LPS antagonist and in negative wells the PBMCs remain unstimulated. Culture supernatants are collected 8, 24 or 48 hours after addition of the LPS and TNF-α IL-1 β and/or other cytokine levels in the culture supernatants are quantitated by commercially available capture ELISAs (R & D Systems).

The efficacy of the adjuvant to enhance an immune response against an antigen can be determined, e.g., by examining the presence and/or the extent of a humoral (antibody) response and/or cell mediated immunity. Assays for measuring humoral and cell mediated responses are known in the art and are also described in Example 3 and, e.g., in PCT/US98/26291 (WO 99/29728). For example, a composition of the present invention containing an LPS antagonist may be tested in mice for the ability to enhance an antibody response to an antigen and the delayed-type hypersensitivity (DTH) response, measured by an increase in footpad swelling after inoculation in the footpad of the test animal, as compared to the measurements in an animal to which the same composition without the LPS antagonist was administered. Each animal in the test group may receive the amount of antigen combined with different amounts of the LPS antagonist. Serum samples are then obtained from each animal after the final inoculation, and the serum is analyzed for the presence of antibodies against the antigen using methods known in the art, e.g., ELISA. DTH responses to the antigen can be measured after the final inoculation (e.g., within 1–7 days). An increase in serum antibodies against the antigen and/or an increase in footpad swelling in the animals having received the antigen together with an LPS antagonist relative to the responses in animals having received the antigen alone indicates that the LPS antagonist is an adjuvant.

5.4 Preparations Comprising a Vaccine Antigen and a Pharmaceutically Active Amount of an LPS Antagonist

5.4.1 Formulation

To formulate preparations comprising a vaccine antigen (for example, a polysaccharide, protein or nucleic acid vaccine) and an LPS antagonist, the optimal dose of each component must first be ascertained. By way of illustration, the optimal dose of vaccine and an LPS antagonist can be determined using a "checkerboard" approach, wherein the dose of LPS and vaccine antigen are varied over a broad range and the optimal dose of each determined by identifying the combination that results in maximal stimulation of host immunity (See Examples herein).

These preparations can be administered by any one of a number of well-known routes of vaccination, including but not restricted to the intradermal, transdermal, topical, subcutaneous, intramuscular, intraperitoneal, intranasal, parenteral (e.g., intravenous) or oral routes. To determine the immunogenicity of the antigen in the absence of an LPS antagonist, groups of laboratory animals are vaccinated with the individual doses of the vaccine antigen formulated alone. The development of humoral and cell-mediated immune responses against the vaccine antigen are measured using standard immunological techniques before vaccination and on days 10, 20, and 30 after vaccination, as described (Coligan, et al., (Eds.) 1994, In: Current Protocols in Immunology, John Wiley and Sons Inc, NY).

The LPS antagonist and the antigen are preferably administered simultaneously as a single composition. The LPS antagonist or antigen can, however, also be administered separately, e.g., consequentially, provided that separate administration results in an increased immune response against the antigen relative to an immune response resulting from administration of the antigen without the LPS antagonist.

The exact amount of such LPS antagonists required will vary from subject to subject, depending on the species, age, weight and general condition of the subject, the severity of the disease that is being treated, the particular compound used, its mode of administration, and the like. Thus, it is not possible to specify an exact amount. However, an appropriate amount may be determined by one of ordinary skill in the art using only routine experimentation given the teachings herein and optimization procedures known in the art. Generally, dosage will approximate that which is typical for suitable LPS antagonist activity and activation of target cells (generally in the ng/kg range), preferably in the range of about 0.0001 mg/patient to 600 mg/patient. More preferable ranges are about 0.001 mg/patient to 350mg/patient. Most preferable ranges are from 0.01 to 100 mg/patient. One skilled in the art, however, could readily elucidate other dosage ranges and regimens and the above are expressly intending to be non limiting.

5.4.2 Vaccine Antigens

As mentioned above, it is envisaged that preparations containing an LPS antagonist can be combined with any vaccine antigen. For the purposes of this invention, the vaccine antigen may comprise, e.g., a polysaccharide, amino acid, peptide, nucleic acid (e.g., DNA or RNA or derivative thereof), or combinations thereof.

In instances in which the vaccine antigen is composed of DNA, the DNA may be either closed circular or linear. The DNA may be derived from a commercially available plasmid (e.g., pCEP4 or pRc/RSV obtained from Invitrogen Corporation (San Diego, Calif.), pXTI, pSG5, pPbac or pMbac obtained from Stratagene (La Jolla, Calif.), pPUR or pMAM obtained from Clontech (Palo Alto, Calif.), or pSV-β-gal obtained from Promega Corporation (Madison, Wis.)), or synthesized either de novo or by adaptation of a publicly or commercially available eukaryotic expression system. The DNA may encode a eukaryotic expression cassette, consisting of a promoter (e.g., the human actin promoter (Morishita, et al., 1991, Biochim. Biophys. Acta, 1090:2216), the HLA class I promoter (Koller and Orr, 1985, J. Immunol., 134:2727), the CMV intermediate early promoter (Thomsen, et al., 1984, Proc. Natl. Acad. Sci. USA, 81:659; Rotondaro, et al., 1996, Gene, 168:195), the SV40 early region and late promoters (Fromm and Berg, 1982, J. Mol. Appl. Genet., 1:457; May, et al., 1987, Nucl. Acids Res., 15:2445; Huang, et al., 1990, Genes Dev., 4:287); sequences encoding at least one gene from a viral, bacterial or parasitic pathogen as described below; transcriptional and translational enhancer sequences (See e.g., May, et al., 1987, supra; Banedji, et al., 1981, Cell, 27:299; Lewin (Ed.), 1998, In: Genes, John Wiley and Sons, NY); and sequences encoding poly-adenosine (Lewin, 1998, supra).

In instances in which the vaccine antigen is composed of RNA, the RNA may contain sequences encoding at least one gene from a viral, bacterial or parasitic pathogen; translational enhancer sequences (e.g., 5' cap translation enhancer (Lewin (Ed.), 1998, supra); a cap independent translation enhancer (CITE) sequence, such as those derived from encephalomyocarditis virus (Duke, et al., 1992, J. Virol., 66:1602); and sequences encoding poly adenosine (Lewin, 1998, supra). Alternatively, the RNA may be composed of an RNA molecule encoding a recombinant Semiliki forest virus vector (Berglund, et al., 1999, Vaccine, 17:497) that expresses a passenger viral, bacterial or parasitic gene; or a recombinant VEE virus vector (Pushko, et al., 1997, Virology, 239:389) that expresses a passenger viral, bacterial or parasitic gene.

The vaccine antigen may be derived from any viral, bacterial or parasitic pathogen which is pathogenic for a human, domestic animal or wild animal, and may be any molecule that is expressed by any viral, bacterial, or parasitic pathogen prior to or during entry into, colonization of, or replication in its host. The vaccine antigen may be given alone or in combination with one or more viral, bacterial, or parasitic antigens.

Alternatively, the vaccine antigen may be a tumor-, transplantation-, or autoimmune specific antigen. These latter vaccine antigens may be given alone or in combination with one or more tumor-, transplantation-, or autoimmune-specific antigens.

The viral pathogens, from which the viral antigens are derived, include, but are not limited to, Orthomyxoviruses, such as influenza virus; Retroviruses, such as RSV; Herpesviruses, such as EBV; CMV or herpes simplex virus; Lentiviruses, such as human immunodeficiency virus; Rhabdoviruses, such as rabies; Picomoviruses, such as poliovirus; Poxviruses, such as vaccinia; Rotavirus; and Parvoviruses.

Examples of vaccine antigens of viral pathogens include the human immunodeficiency virus antigens Nef; p24; the Env proteins gp 120, gp 160, and gp41; Tat; Rev; Gag; Vif; and Pol (Hahn, et al., 1985, Nature, 313:277–280) and T cell and B cell epitopes of gp120 (Palker, et al., 1989, J. Immunol., 142:3612–3619). Other vaccine antigens include the hepatitis B surface antigen (Wu, et al.: 1.989, Proc. Natl. Acad. Sci., USA, 86:4726–4730); rotavirus antigens, such as VP4 (Mackow, et al., 1990, Proc. Natl. Acad. Sci., USA, 87:518–522) and VP7 (Green, et al., 1988, J. Virol. 62:1819–1823), influenza virus antigens such as hemagglutinin or nucleoprotein (Robinson, et al., supra, Webster, et al., supra) and herpes simplex virus thymidine kinase (Whitley, et al., In: New Generation Vaccines, p.825–854).

The bacterial pathogens, from which the bacterial antigens are derived, include but are not limited to, Mycobacterium spp., *Helicobacter pylori*, Salmonella spp., Shigella spp., *E. coli* Rickettsia spp., Listeria spp., *Legionella pneumoniae*, Pseudomonas spp., Vibrio spp., and *Borellia burgdorferi*.

Examples of vaccine antigens of bacterial pathogens include the capsular polysaccharide of *Neisseria meningitis* (Goldblatt, 1998, Med. Microbiol., 47:563; Nieminen, et al., 1998. Vaccine, 16:630; Rennels, et al., 1998, Pediatrics, 101:604), the Vi polysaccharide of *Salmonella enterica* serovar *typhi* (Robbins and Robbins, 1984, J. Infect. Dis., 150:436; Klugman, et al., 1996, Vaccine, 14:435; Teddy, et al., 1999, Vaccine, 17:110), *Shigella sonnei* form 1 antigen (Formal, et al., 1981, Infect. Immun., 34:746–750); the O-antigen of *V. cholerae* Inaba strain 569B (Forrest, et al., 1989, J. Infect. Dis., 159:145–146); cholera toxin of *V. cholerae* (Finkelstein, 1992, In D. Barua and E. B. Greenough III (Eds.) Current Topics in Infectious Disease: Cholera. Plenum Pub. Co NY); TCP of *V. cholerae* (Finkelstein, 1992, supra); CFA/I fimbrial antigen of enterotoxigenic *E. coli* (Yamamoto, et al., 1985, Infect. Immun, 50:925–928); the heat-labile toxin of *E. coli* (LT; Clements, et al., 1984, 46:564–569); pertactin of *Bordetella pertussis* (Roberts, et al., 1992, Vaccine, 10:43–48); adenylate cyclase-hemolysin of *B. pertussis* (Guiso, et al., 1991, Micro. Path., 11:423–431); fragment C of tetanus toxin of *Clostridium tetani* (Fairweather, et al., 1990, Infect. Immun., 58:1323–1326).

The parasitic pathogens, from which the parasitic antigens are derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofalaria spp., Wuchereria spp., and Onchocerea spp.

Examples of vaccine antigens of parasitic pathogens include the circumsporozoite antigens of Plasmodium spp. (Sadoff, et al., 1988, Science; 240:336–337), such as the circumsporozoite antigen of *P. besghei* or the circumsporozoite antigen of *P. falciparum*; the merozoite surface antigen of Plasmodium spp. (Spetzler, et al., 1994, lnt. J. Pept. Prot. Res., 43:351–358); the galactose specific lectin of *Fntamoeba histolylica* (Mann, et al., 1991, Proc. Natl. Acad. Sci., USA, 88:3248–3252), gp63 of Leishrnnia spp. (Russell, et al., 1988, J. Immunol., 140:1274–1278), paramyosin of *Brugio rnalayi* (Li, et al., 1991, Mol. Biochem. Parasitol., 49:315–323), the triose-phosphate isomerase of *Sclristosorna rnansoni* (Shoemaker, et al., 1992, Proc. Natl. Acad. Sci., USA, 89:1842–1846); the secreted, lobin-like protein of *Trichostrongylus colubrqjcrmis* (Frenkel, et al., 1992, Mol. Biochem. Parasitol., 50:2 7–36); the glutathione-S-transferase of *F'rasciola hepatica* (Hillyer, et al., 1992, Exp. Parasito:., 7 5:176–186), *Schistosoma bovis* and *S. japonicum* (Bashir, et al., 1994, Trop. Geog. 1led 46:255–258); and KLH of *Schisiosoma bovis* and *S. japonicum* (Bashir, et al., 1994, supra).

Examples of tumor specific antigens include but are not restricted to prostate specific antigen (Gattuso, et al., 1995, Human Pathol., 26:123), TAG-72 and carcinoembrionic antigen (CEA) (Kris, et al., 1999, Cancer Res., 59:676; Guadagni, et al., 1994, Int. J. Biol. Markers, 9:53), MAGE-1 and tyrosinase (Coulie, et al., 1993, J. Immunother., 14:104); mutant p53 antigen (Mayordomo, et al., 1996, J. Exp. Med., 183:1357). Recently it has been shown in mice that immunization with non-malignant cells expressing a tumor antigen provides a vaccine effect by inducing an immune response that clears malignant tumor cells displaying the same antigen (Koeppen, et al., 1993, Anal. N.Y. Acad. Sci., 690:244).

Examples of transplant antigens include the CD3 receptor on T cells (Alegre, et al., 1995, Digest. Dis. Sci., 40:58–64). Treatment with an antibody to CD3 receptor has been shown to rapidly clear circulating T cells and reverse most rejection episodes (Alegre, et al., 1995, supra).

Examples of autoimmune antigens include IAS β chain (Topham, et al., 1994, Proc. Natl. Acad. Sci., USA, 91:8005–8009). Vaccination of mice with an 18 amino acid peptide from IAS β chain has been demonstrated to provide protection and treatment to mice with experimental autoimmune encephalomyelitis (Topham, et al., 1994, supra).

Alternatively, the present invention allows for the inclusion of immune-stimulatory molecules in the above described preparations, such as growth factors and cytokines. These immunostimulatory molecules include, but are not limited to, growth factors, such as M-CSF, UM-CSF and cytokines, such as IL-2, IL-4, IL-5, IL-6. IL-10, IL-12 or IFN-γ (Nossal, 1999, supra; Vogel and Powell, 1995, supra; Nash, et al., 1993, supra; Pardoll, 1995, supra; Kurane, et al., 1997, supra; Tagliabue and Boraschi, 1993, supra; Lofthouse, et al., 1995, supra; Pasquini, et al., 1997, supra; Jankovic, et al., 1997, supra).

5.4.3 Combination Therapy

According to a specific embodiment of the present invention, an LP S antagonist, may optionally be used in combination with other therapeutic agents to enhance the antiviral effect achieved.

In an exemplary embodiment, an LPS antagonist is used in combination with an antiviral agent. Such antiviral agents which may be used with a preparation of an LPS antagonist include but are not limited to those which function on a different target molecule involved in viral replication, e.g., reverse transcriptase inhibitors (e.g., azidothymidine (AZT), lantivudine (3TC), deoxyinosine (ddI), and dideoxycytidine (ddC)), viral protease inhibitors, glycosylation inhibitors; those which act on a different target molecule involved with viral transmission; those which act on a different loci of the same molecule; and those which prevent or reduce the occurrence of viral resistance. One skilled in the respective art would know of a wide variety of antiviral therapies which exhibit the above modes of activity for a given virus.

An LPS antagonist can also be used in combination with retrovirus inhibitors, such as nucleoside derivatives. Nucleoside derivatives are modified forms of purine and pyrimidine nucleosides which are the building blocks of RNA and DNA. Many of the nucleoside derivatives under study as potential anti-HIV medications, for example, result in premature termination of viral DNA replication before the entire genome has been transcribed. These derivatives lack 3' substituents that can bind to subsequent nucleosides and result in chain termination. Nucleoside derivatives such as 3' azido-3'-thymidine (AZT) and dideoxyinosine (ddI) have been exploited as inhibitors of HIV-1 replication, both in vitro and in vivo. Nucleoside analogs are currently the only licensed therapeutics for the treatment of HIV infection and AIDS (Fischl, et al., 1987, N. Engl. J. Med., 317:185; Mitsuya and Broder, 1987, Nature, 325:773). This class of compounds works by inhibiting reverse transcriptase resulting in a block in cDNA synthesis (Mitsuya and Broder, 1987, supra), these inhibitors work early in the infectious cycle of HIV-1 and inhibit integration into T-cell genome.

Further, a preparation of reduced or absent pyrogenicity of LPS or lipid A can be used in combination with nucleoside derivatives which include but are not limited to, 2',3' dideoxyadenosine (ddA); 2',3'-dideoxyguanosine (ddG); 2',3'-dideoxyinosine (ddI); 2',3' dideoxycytidine (ddC); 2',3'-dideoxythymidine (ddT); 2',3'-dideoxy-dideoxythymidine (d4T) and 3'-azido-2',3'-dideoxythymidine (AZT). Alternatively, halogenated nucleoside derivatives may be used, preferably 2',3'-dideoxy-2'-fluoronucleosides including, but not limited to, 2',3'-dideoxy 2'-fluoroadenosine; 2',3'-dideoxy-2'-fluoroinosine; 2',3'-dideoxy-2'-fluorothymidine: 2',3'-dideoxy 2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T). Preferably, the 2',3'-dideoxy-2' fluoronucleosides of the invention are those in which the fluorine linkage is in the beta configuration, including, but not limited to, 2'3'-dideoxy-2'-beta-fluoroadenosine (F-ddA), 2',3' dideoxy-2'-beta-fluoroinosine (F-ddI), and 2',3'-dideoxy-2'-beta-fluorocytosine (F-ddC). Such combinations allow one to use a lower dose of the nucleoside derivative thus reducing the toxicity associated with that agent, without loss of antiviral activity because of the use of the LPS antagonist. Moreover, such a combination reduces or avoids viral resistance.

According to the present invention, preparations of LPS antagonist can also be used in combination with uridine phosphorylase inhibitors, including but not limited to acyclouridine compounds, including benzylacyclouridine (BAU); benzyloxybenzylacyclouridine (BBAU); aminomethyl-benzylacyclouridine (AMBAU); aminomethyl-benzyloxybenzylacyclouridine (AMB-BAU); hydroxymethyl-benzylacyclouridine (HMBAU); and hydroxymethyl benzyloxybenzylacyclouridine (HMBBAU).

According to the present invention, preparations of LPS antagonist can be used in combination with viral protease inhibitors, including but not limited to, Invirase (saquinavir, Roche), ABT-538 (Abbott, CAS Reg. No. 155213-67-5), AG1343 (Burroughs Wellcome/Glaxo, CAS Reg. No. 161814-49-9). Protease inhibitors are generally thought to work primarily during or after assembly (i.e., viral budding) to inhibit maturation of virions to a mature infectious state. For example, ABT-538 has been shown to have potent antiviral activity in vitro and favorable pharmokinetic and safety profiles in vivo (Ho, et al., 1995, Nature, 373:123). Administration of ABT-538 to AIDS patients causes plasma HIV-1 levels to decrease exponentially and CD4 lymphocyte counts to rise substantially. The exponential decline in plasma viraemia following ABT-538 treatment reflects both the clearance of free virions and the loss of HIV-1 producing cells as the drug substantially blocks new rounds of infection. ABT-538 treatment reduces virus mediated destruction of CD4 lymphocytes. Combining this treatment with a preparation of LPS antagonist, which inhibits at an earlier stage of HIV infection, viral fusion, would be likely to have synergistic effects and have a dramatic clinical impact.

In order to evaluate potential therapeutic efficacy of U IS antagonist in combination with the antiviral therapeutics described above, these combinations may be tested for antiviral activity according to methods known in the art.

A compound of the invention can be administered to a human patient by itself or in pharmaceutical compositions where it is mixed with suitable carriers or excipients at doses to treat or ameliorate various conditions involving viral infection. A therapeutically effective dose further refers to that amount of the compound sufficient to inhibit viral infection. Therapeutically effective doses may be administered alone or as adjunctive therapy in combination with other treatments for viral infection or associated diseases. Techniques for the formulation and administration of the compounds of the instant application may be found in "Remington's Pharmaceutical Sciences" Mack Publishing Co., Easton, Pa., latest addition.

In another embodiment, viral infection is treated or prevented by administration of a Therapeutic of the invention in combination with one or more chemokines. In particular, the Therapeutic is administered with one or more C-C type chemokines, especially one or more from the group consisting of RANTES, MIP-1α and MIP-1β (see, e.g, WO 99/2978 by Gallo et al.).

5.4.4 Monitoring Effects of an LPS Antagonist During Clinical Trials

The treatment of an individual with an LPS antagonist can be monitored by determining LPS antagonist characteristics, such as LPS antagonist level or activity (e.g., fever, IL-1 and/or IL-6 production, acute phase reactant production), IL-1, TNF α and/or IL-6 mRNA levels, and/or transcription levels. Clinical tests useful for testing the efficacy of the treatment are well known in the art and include ELISA, Northern blot, RT-PCR, etc. These measurements indicates whether the treatment is effective or whether it should be adjusted or optimized.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a preadministrarion sample from a subject prior to administration of the LPS antagonist; (ii) detecting the LPS antagonist or an activity thereof in the preadministration sample; (iii) obtaining one or more post-administration samples from the subject; (iv) detecting the level of the LPS antagonist or an activity thereof in the post-administration samples; (v) comparing the level of the LPS antagonist or activity thereof in the preadministration sample with that in the post administration sample or samples; and (vi) altering the administration of the agent to the subject accordingly. For example, increased administration of the agent may be desirable to increase the level of LPS antagonizing activity or to increase the immune response to a co-administered antigen, i.e., to increase the effectiveness of the agent. Alternatively, decreased administration of the agent may be desirable to decrease LPS antagonist activity, i.e., to decrease the effectiveness of the agent.

Cells of a subject may also be obtained before and after administration of an LPS antagonist to detect the level of expression of genes that respond to an LPS antagonist, to verify that the LPS antagonist does not increase or decrease the expression of genes which could be from cells exposed in vivo to an LPS antagonist and mRNA from the same type of cells that were not exposed to the LPS antagonist could be reverse transcribed and hybridized to a chip containing DNA from numerous genes, to thereby compare the expression of genes in cells treated and not treated with an LPS antagonist. If, for example, an LPS antagonist turns on the expression of a proto-oncogene in an individual, use of this particular LPS antagonist may be undesirable.

5.4.5 Kits

The invention further provides kits for administration of an adjuvant of the invention with a vaccine antigen to a subject and/or for monitoring the level of adjuvant or its toxicity in a subject.

In one embodiment, the kit comprises an LPS antagonist. The kit can further comprise a vaccine antigen. The kit can also comprise an agent for detecting the LPS antagonist, such as an antibody. In another embodiment, the kit comprises an agent which detects an activity of an LPS antagonist, such as the level of a cytokine, e.g, TNF-α, IL1 or IL-6. A kit may also contain standard solutions or graphics (e.g., charts), including positive and negative controls.

A kit of the invention may also provide reagents for detecting ablionnal levels, form or activity of an LPS antagonist, or a breakdown product of an LPS antagonist. In an embodiment of the invention the kit detects autoantibodies specific for an LPS antagonist. These reagents may be labeled.

The components of the kit can be packaged in a suitable container. The kit can further comprise instructions for using the reagents of the kit.

5.4.6 Methods of Treatment

The methods and compositions of the invention may be used as a vaccine in a subject in which immunity for the antigen(s) is desired. Such antigens can be any antigen known in the art to be useful in a vaccine formulation. The methods and compositions of the present invention can be used to enhance the efficacy of any vaccine known in the art. The vaccine of the present invention may be used to enhance an immune response to infectious agents and diseased or abnormal cells, such as, but not limited to, bacteria, parasites, fungi, viruses, tumors, and cancers. The compositions of the invention may be used to either treat or prevent a disease or disorder amenable to treatment or prevention by generating an immune response to the antigen provided in the composition. In one preferred embodiment, the antigen (s) are proteins, fragments or derivatives, including truncation isoforms thereof, encoded by any genes of the HIV genome including the env, gag, pol, nef, vif, rev, and tat genes. In a more preferred embodiment, the antigen is an HIV-associated gp120 protein.

Diseases and disorders that can be treated according to the invention include viral infections, such as an infection by HIV, CMB, hepatitis, herpes virus, measles virus; bacterial infections; fungal and parasitic infections; cancers; autoimmune diseases; and any other disease or disorder amenable to treatment or prevention by eliciting an immune response against a particular antigen or antigens.

The methods and compositions of the present invention may be used to elicit a humoral and/or a cell-mediated response against the antigen(s) of the vaccine in a subject. In one specific embodiment, the methods and compositions elicit a humoral response against the administered antigen in a subject. In another specific embodiment, the methods and compositions elicit a cell med;;zted response against the administered antigen in subject. Preferably both a humoral and a cell-mediated response is triggered.

The subjects to which the present invention is applicable may be any mammalian or vertebrate species, which include, but are not limited to, cows, horses, sheep, pigs, fowl (e.g., chickens), goats, cats, dogs, hamsters, mice, rats, monkeys, rabbits, chimpanzees, and humans. In a preferred embodiment, the subject is a human.

5.4.7 Effective Dose

Toxicity and therapeutic efficacy of the LPS antagonist can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. LPS antagonists which exhibit large therapeutic indices are preferred. While LPS antagonists that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.4.8 Formulation and Use

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, eye drops, injection, inhalation or insufflation either through the mouth or the nose, or oral, buccal, parenteral or rectal administration.

For such therapy, the compounds of the invention can be formulated for a variety of modes of administration, including systemic and topical or localized administration. Techniques and formulations generally may be found in Rentmington's Pharmaceutical Sciences. Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included. The agent can be alternatively administered intravascularly, such as intravenously (IV) or intraarterially.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

For example, for solid compositions, conventional non-toxic solid carriers include pharmaceutical grades of mannitol, lactose, starch, magnesium stearate, sodium saccharin, talc, cellulose, glucose, sucrose, magnesium carbonate, and the like. Liquid pharmaceutically administratable compositions can, for example, be prepared by dissolving, dispersing, etc. an active compound as described herein and optional pharmaceutical adjuvants is an excipient, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences (latest edition).

The LPS antagonist may be administered alone or in combination with other molecules known to have a beneficial effect, such as to enhance the immune response to an antigen (e.g., adjuvant activity), molecules capable of tissue repair and regeneration and/or inhibiting inflammation. Examples of useful cofactors include chemokines (see WO 99/29728). Other useful cofactors include symptom-alleviating cofactors, including antiseptics, antibiotics, antiviral and antifungal agents and analgesics and anesthetics. In addition, substances that enhance the stability and/or activity of the LPS antagonist may be co-administered, either together or sequentially, with the LPS antagonist. In yet another embodiment, the co-factor is an antagonist to any deleterious activity or side-effect of the LPS antagonist.

The LPS antagonist also may be associated with means for targeting the LPS antagonist to a desired tissue. For example, an antibody or other binding protein that interacts specifically with a surface molecule on the desired target tissue cells may be used. Such targeting molecules further may be covalently associated to the LPS antagonist, e.g., by chemical crosslinking, or by using standard genetic engineering means to create, for example, an acid labile bond such as an Asp-Pro linkage. Useful targeting molecules may be designed, for example, using the simple chain binding site technology disclosed, for example, in U.S. Pat. No. 5,091,513.

Preparations, e.g., those for oral administration, may be suitably formulated to give controlled release of the active compound and can be embedded in a slow release matrix for that purpose. For buccal administration, the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via. a coronary catheter into any selected part of the body, without causing inflammation or ischemia. The administered therapeutic is slowly released from these microspheres and taken up by surrounding tissue cells.

Systemic administration can also be by transmacosal or transdermal means. For transmucosal or transdermal administration, penetrants appropriate to the barrier to be permeated are used ire the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compounds of the invention are formulated into ointments, salves, gels, or creams as generally known in the art.

In clinical settings, a gene delivery system for the gene encoding a therapeutic or vaccine antigen can be introduced into a patient in conjunction with the LPS antagonist by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter or by stereotactic injection.

The compositions may, if desired, be presented in a pack or dispenser device which may contain one or more unit dosage forms containing the active ingredient and an LPS antagonist. The pack may for example comprise metal or plastic foil, such as a blister pack. The pack or dispenser device may be accompanied by instructions for administration.

The practice of the present invention can employ, unless otherwise indicated, conventional techniques of cell biology, cell culture, molecular biology, transgenic biology, microbiology, recombinant DNA, and immunology, which are within the skill of the art. Such techniques are explained fully in the literature.

The present invention is further illustrated by the following examples which should not be construed as limiting in any way. The contents of all cited references (including literature references, issued patents, published patent applications as cited throughout this application) are hereby expressly incorporated by reference.

6. EXEMPLIFICATION

The following Examples are provided for illustrative purposes only, and are in no way intended to limit the scope of the present invention.

6.1 Example 1

Preparation of Non-Pyrogenic LPS from E. coli Double Mutant MLK986

This Example describes the production and purification of non-pyrogenic LPS antagonist from MLK986 for use as adjuvant.

6.1.1 Bacterial Cell Culture

Strain MLK986 was cultured on solid medium at 37° C. prior to seeding the liquid media. A one liter liquid culture (1 L) was seeded the following day at a starting inoculum of about $1\times10^4$ cfu/ml and grown for 16 hours at 37° C. with shaking (2500 pm).

6.1.2 Isolation and Purification of LPS

The liquid culture was harvested by centrifugation at 7000×g for 10 minutes, washed once in 250 ml endotoxin-free irrigation saline (Baxter) and the weight of the bacterial pellet was determined. The pellets was then resuspended in endotoxin-free water (Baxter) at a final density of 2% w/v±0.25%. Subsequently, LPS was isolated by two cycles of hot-water phenol extraction. In short, the bacterial suspension was heated to 70° C. to which an equal volume of pre-warmed phenol was added and mixed for 15 minutes at 70° C. The mixture was cooled to 25° C. and then centrifuged at 18,000×g for 15 minutes. Following this centrifugation the aqueous phase was removed, placed into dialysis tubing (SpectraPor) and dialyzed against running distilled $H_2O$ overnight. The retentate was then placed into fresh 50 ml polypropylene tubes and treated with RNaseA (100 mg/ml) at 37° C. for 1 hour, followed by DNaseI (50 mg/ml and 5 mM $MgCl_2$) at 37° C. for 1 hour, followed by Pronase (250 mg/ml) at 37° C. for 1 hour. Then EDTA was added to a final concentration of 5 mM and the hot-water phenol extraction procedure described above was repeated. Following dialysis, the retentate was centrifuged at 20,000×g for 15 minutes al 4° C. The supernatants were transferred to fresh Beckman 50Ti tubes and the LPS was pelleted by centrifugation at 110,000×g for 2 hours at 4° C. The supernatants were discarded and the pellets were vacuum dried. The LPS preparation was evaluated for DNA and protein contamination by SDS-PAGE and silver stain, BCA protein estimate assay and UV spectrophotometry.

6.1.3 LPS Antagonistic Activity of MLK986 LPS

To confirm that MLK986 LPS possesses LPS antagonist activity, MLK986 LPS (cultured at 37° C.) at 1 µg/ml was mixed with varying amounts of W3110 LPS (also obtained from bacteria grown at 37° C., and isolated as described above for MLK986 LPS) from 1 ng/ml to 100 ng/ml and these mixtures were used to stimulate human peripheral blood mononuclear cells (PBMCs). W3110 LPS (also cultured at 37° C.) from 1 ng/ml to 100 ng/ml alone and W3110 LPS (10 ng/ml) mixed with synthetic lipid $IV_A$ (1 µg/ml) were used as controls. For this, PBMCs were obtained from 50 ml of whole blood and resuspended in complete medium (CM; RPMI containing pyruvate, glutamine, PenStrep, and 10% endotoxin-free human AB serum (Life Technologies) at a density of $6\times10^6$ PBMCs/ml. CM containing W3110 LPS, MLK986 LPS or synthetic lipid $IV_A$ was placed into duplicate wells of a 96-well flat bottom culture plate (Costar) at double the target final concentration. An equal volume of CM containing the PBMCs then was added to these wells and the culture plates were incubated at 37° C. in 5% $CO_2$ for 8 hr. The supernatants were then removed and stored at 70° C. Quantitation of TNFα, IL-1β, and IL-6 in these culture supernatants was achieved by capture ELISA (R&D Systems).

The level of TNFα in culture supernatants collected 8 hr after stimulation shows that W3110 LPS at a concentration of 1 ng/ml and above elicited TNFα secretion, but that MLK986 LPS significantly antagonized this response (Table 1). Interestingly, LPS from MLK986 cultured at 42° C. produced did not display LPS antagonist activity. Since culture temperature has been shown to influence LPS aggregation and influence LPS activity (Shnyra et al., 1993, *Infection and Immunity* 61:5351–5360), this later finding may be due to differential aggregation properties of MLK986 LPS produced under the distinct culture conditions.

TABLE 1

LPS antagonist properties of MLK986 LPS

| Treatment | TNFa (pg/ml) |
| --- | --- |
| W3110 (100 ng/ml) | 1404 ± 40 |
| W3110 (10 ng/ml) | 1192 ± 37 |
| W3110 (1 ng/ml) | 536 ± 178 |
| MLK986/37° C. (1 μg/ml) | <30 |
| MLK986/37° C. (1 μg/ml) + W3110 (100 ng/ml) | <30 |
| MLK986/37° C. (1 μg/ml) + W3310 (10 ng/ml) | <30 |
| MLK986/37° C. (1 μg/ml) + W3110 (1 ng/ml) | <30 |
| Lipid $IV_A$ (1 μg/ml) + W3110 (10 ng/ml) | <30 |

6.2 Example 2

Increased Immunogenicity of a Peptide Antigen

This Example demonstrates the potent adjuvant activity of an LPS antagonist when administered together with a peptide antigen to an animal.

Vaccine preparations containing a peptide antigen and an LPS antagonist were prepared in the following manner. Each vaccine preparation contained 50 mg of the vaccine peptide (herein designated "Hep-Tat") that corresponds to the heparin-binding domain of the HIV-1 regulatory protein Tat and is comprised of the following sequence (GLGIS YGRKKRRQR; SEQ ID NO: 1). The peptide antigen was prepared synthetically as a Multiple Antigen Peptide (MAPS;Genosys). To formulate the preparations comprised of Hep-Tat and LPS antagonist (purified as outlined above), 50 mg of Hep-Tat was combined with a range of LPS antagonist doses (from 1 mg to 10 mg). The LPS antagonist was isolated from MLK986 cultured at 37° C. as described in. Example 1. The dose of peptide was chosen from preliminary experiments in which 50 mg of Hep-Tat was found to be marginally immunogenic when formulated with Alum (Pierce) as an adjuvant.

Groups of three BAL Blc mice were injected intraperitoneally with a single dose of a given preparation of Hep-Tat and LPS antagonist (i.e., primary vaccination). To determine the immunogenicity of the antigen in the absence of LPS antagonist, a group of BALB/c mice were vaccinated with 50 μg Hep-Tat formulated-alone. For comparative purposes, an additional group of mice was vaccinated with 50 μg Hep-Tat formulated with Alum, as described (Coligan, et al., 1994, supra).

To measure the immunogenicity of each formulation, venous blood was collected from the mice in each group before and on day 14 after primary vaccination, as described (Coligan, et al., 1994, supra). Serum was then obtained from each of these blood samples using standard techniques (Coligan, et al., 1994, supra). On day 21 after the primary vaccination, mice were given a booster vaccination containing the same dose of Hep-Tat and LPS antagonist or alum as was given in the primary vaccination. Seven days after the boost, venous blood was collected from the mice in each, and sera were obtained as outlined above. Each of the serum samples from individual groups were pooled and the level of Hep-Tat-specific IgG was ascertained by ELISA. In short, plastic 96 well ELISA plates (Immunol 2 Dynatech) were coated with Hep-Tat, by adding 50 μg of Hep-Tat at 10 μg/ml suspended in PBS (Phosphate Buffer Saline) pH 7.4 in each well, and incubating overnight at 4° C. The plates were subsequently washed to remove unbound peptide and then 100 μl of blocking solution (comprised of 1% (w/v) Bovine Serum Albumin (BSA; Sigma) suspended in PBS) was added to each well. After incubating the plates for 1 hour at 25° C., the blocking solution was removed and 3-fold serial dilutions of the sera (suspended in PBS containing 1% BSA and 0.5% Tween-20 (Sigma) from the vaccinated mice were added to each well. The plates were then incubated for a further 1 hour at 25° C. and then washed thoroughly 4 times with PBS containing 0.5% Tween-20. Then, 100 μl of goat anti-mouse IgG antibody conjugated to horse radish peroxidase (from Sigma and diluted 1:2000 in PBS containing 1% BSA) was added to each well. The plates were incubated for 1 hour at 25° C. The plates were then, washed thoroughly a further 4 times with PBS containing 0.5% Tween-20 to remove unbound anti-mouse antibody and then 100 μl of substrate was added to each well. The plates were then incubated for a further 30–60 minutes. Further degradation of the substrate was terminated by adding stopping solution. The result of the ELISA were obtained by reading the optical density of each well using a Molecular Dynamics ELISA plate reader. The data, shown in Table 2, are presented as dilution of the sera to achieve the 50% saturation.

TABLE 2

Induction of Tat-specific antibodies

| Group | Formulation | Pre | Day 14 | Day 21 |
| --- | --- | --- | --- | --- |
| 1 | 50 μg Hep-Tat alone | <10 | <10 | <10 |
| 2 | 50 μg Hep-Tat + 1 μg LPS antagonist | <10 | 20 | 300 |
| 3 | 50 μg Hep-Tat + 3 μg LPS antagonist | <10 | 30 | 3000 |
| 4 | 50 μg Hep-Tat + 10 μg LPS antagonist | <10 | 30 | 3000 |
| 5 | 50 μg Hep-Tat + Alum (50% v/v) | <10 | <10 | <10 |

The results of this experiment showed that the LPS antagonist augmented the Hep-Tat specific antibody response and that the optimum adjuvant effect of the LPS antagonist (defined herein as the lowest dose of adjuvant required to induce an immune response against the antigen) when formulated with Hep-Tat was 3 μg. Furthermore, these data show that said LPS antagonist is significantly more effective as an adjuvant than Alum.

A similar adjuvant effect can be obtain in dogs, rabbits, guinea pigs, chickens and rats using the above outlined approach and injecting the preparations containing Hep-Tat and LPS antagonist subcutaneously, intramuscularly or intranasally.

6.3 Example 3

Increased Immunogenicity of a Praiein Antigen

This Example demonstrates the potent adjuvant activity of an LPS antagonist when administered together with a protein antigen to an animal.

Vaccine preparations containing an LPS antagonist and a protein antigen can be prepared in the following manner. Each vaccine preparation contained 5 μg of fully glycosylated endotoxia-free HIV-1$_{MN}$ gp120 (Virostat Cat. No. 8919, Lot AM735). Preparations comprised of gp120 and LPS antagonist were formulated essentially as outlined in Example 2 above except that each dose contained 5 μg of gp120 combined with a range of LPS antagonist doses (from 1 μg to 10 μg). The LPS antagonist was isolated from MLK986 cultured at 37° C. as described above. The dose of gp120 was chosen from preliminary experiments that determined this dose to be marginally immunogenic when formulated with Alum as an adjuvant.

Groups of 3 BALB/c mice were given a single dose of a given preparation of gp120 and LPS antagonist subcutaneously (primary vaccination). To determine the immunogenicity of the antigen in the absence of LPS antagonist, a group of BALB/c mice were vaccinated with 5 μg gp 120 formulated alone. For comparative purposes, an additional group of mice were vaccinated with 5 μg of gp120 formulated with Alum, as described (Coligan, et al., 1994, supra).

To measure the immunogenicity of each formulation, sera were collected from the mice in each group before and on day 14 after primary vaccination, as described in Example 2 above. On day 21 after the primary vaccination, mice were given a booster vaccination containing 10 μg of gp120 formulated with matched doses of LPS antagonist, as was given in the primary vaccination. Ten and 17 days after the boost, venous blood was collected from the mice, and sera were obtained as outlined above. The level of anti-gp120 IgG in pooled serum samples was determined by ELISA as described in Example 2 above, except that gp120 was used in place of Hep-Tat in the first coating step. The results of the ELISA were obtained by reading the optical density of each well using a Molecular Dynamics ELISA plate reader and are shown in Table 3 below. The data are presented as dilution of the sera to achieve 50% saturation.

TABLE 3

Induction of Gp120-specific Serum Antibodies

| Group | Formulation | Pre | Day 14 | Day 21 |
|---|---|---|---|---|
| 1 | Gp 20 alone | −10 | <10 | <10 |
| 2 | Gp120 + 1 μg LPS antagonist | <10 | <10 | 20 |
| 3 | Gp120 + 3 μg LPS antagonist | <10 | <30 | 30 |
| 4 | Gp120 + 10 μg LPS antagonist | <10 | <10 | 100 |
| 5 | GP120 + Alum (50% v/v) | <10 | <10 | 20 |

The results of this experiment showed that the LPS antagonist augmented the gp120specific response and that the optimum adjuvant effect of the LPS antagonist (defined herein as the lowest dose of adjuvant required to induce an immune response against the antigen) when formulated with gp120 was 10 μg. Furthermore, these data concur with the data in Example 2 and show that the LPS antagonist is significantly more effective as an adjuvant than Alum.

To further measure the adjuvant activity of the LPS antagonist, the level of HIV-1 gp120-specific T cell proliferation was quantitated using a conventional $^3$H-thymidine-incorporation assay (Wu, et al., 1997, AIDS Res. Human Retrovirus, 13:1187). Spleen cells were harvested 28 days after the final vaccination and stimulated with bovine serum albumin (10 μg/ml) or purified recombinant gp 120 (10 μg/ml). The stimulated cells and matched unstimulated control cells were incubated for three days at 37° C. in a 5% $CO_2$ incubator. At this time, $^3$H-thymidine was added to each well and the cells were incubated for a further 48 hours, as described in Wu, et al., 1997, supra).

The level of $^3$H-thymidine incorporation was calculated by subtracting the $^3$H-thymidine incorporated. in unstimulated control wells and the results were expressed as the net $^3$H-thymidine incorporation. The results are shown in Table 4.

TABLE 4

Gp120-specific T Cell Proliferation

| Adjuvant | BSA @ 10 μg/ml | Gp120 @ 10 μg/ml (Fold increase) |
|---|---|---|
| Alum (50% v/v) | 9410* | 8549 (0) |
| LPS antagonist (1 μg/ml) | 8489 | 14232 (1.7) |
| LPS antagonist (3 μg/ml) | 6018 | 31296 (5.2) |
| LPS antagonist (10 μg/ml) | 6682 | 20992 (3.1) |

*The values shown are expressed as the net $^3$H-thymidine incorporation in counts per minute The results of this assay show that the LPS antagonist is a strong adjuvant for use with protein antigens and that it is more effective at enhancing T cell responses than Alum.

A similar adjuvant effect can be obtained in dogs, rabbits, guinea pigs, chickens and rats using the above outlined approach and injecting the preparations containing gp120 and LPS antagonist subcutaneously, intramuscularly or intranasally.

6.4 Example 4

Increased Immunogenicity of a DNA Vaccine

This Example demonstrates the potent adjuvant activity of an LPS antagonist when administered together with a DNA vaccine to an animal.

Vaccine preparations containing a vaccine antigen and an adjuvant were prepared in the following manner. Each vaccine preparation contained 5 mg of endotoxin-free plasmid DNA, herein designated pSF128.2, which expresses HIV-1$_{Ba-L}$ gp140 (Reitz, et al., 1994, AIDS Res. Hum. Retroviruses, 10:621; Ivey-Hoyle, et al., 1991, Proc. Natl. Acad. Sci. USA, 88:512) under the control of the CMV immediate early promoter. HIV-1$_{Ba-L}$ gp140 is an important HIV-1 vaccine target. This envelope derivative is expressed in a soluble form, yet it forms an oligomeric structure that contains discontinuous epitopes that are present on the native envelope structure (Stamatos, et al., 1998, J. Virol., 72:9656). Preparations comprising pSF128.2 and LPS antagonist were formulated essentially as outlined in Example 2 above except that each dose contained 5 mg of pSF128.2 combined with a range of LPS antagonist doses (from 1 mg to 30 mg; see Table 4). The LPS antagonist was isolated from MLK986 cultured at 37° C., as described above.

Groups of 3 BALB/c mice were given a single dose of a given preparation of pSF 128.2 and LPS antagonist intramuscularly (primary vaccination). Four weeks after vaccination the mice were boosted with 10 µg of purified recombinant gp140 also formulated with LPS antagonist. The amount of LPS antagonist used in the booster vaccines was matched to the amount used in the DNA vaccine; the dose of the booster antigen used was insufficient by itself to induce a measurable immune response against gp140. Thus, this strategy provided an efficient method for measuring the priming effect of the DNA vaccine formulations. To determine the immunogenicity of the pSF128.2 in the absence of LPS antagonist, a group of 3 BALB/c mice was vaccinated with µg pSF128.2 and boosted 4 weeks later with 10 µg of gp140 formulated alone. For comparative purposes, an additional group of mice was vaccinated with 5 µg of pSF 128.2 DNA formulated with 50 µg of monophosphoryl-lipid A (MPLA; Ribi Immunochem Research), as described (Sasaki, et al., 1997, Infection and Immunity 65:3520–3528) and boosted 4 weeks later with 10 µg of gp140 formulated with 50 µg of MPLA.

To measure the immunogenicity of each formulation, sera were collected from the mice in each group before and on days 14 and 60 after primary vaccination, as described in Example 2 above. The level of anti-HIV-1 gp140 Env IgG in pooled serum samples was determined by ELISA as described in Example 2 above, except that purified HIV-1$_{Ba-L}$ gp140 was used in the place of Hep-Tat in the first coating step. The results of the ELISA were obtained by reading the optical density of each well using a Molecular Dynamics ELISA plate reader and are shown in Table 5.

TABLE 5

LPS antagonist elevates the immunogenicity of DNA vaccines

| Adjuvant | Priming Vaccine (Day 0) | Gp140-specific Serum IgG titer (Day 14) | Booster Vaccine (Day 28) | Gp140-specific Serum IgG titer (Day 60) |
|---|---|---|---|---|
| None | None | <30 | None | <30 |
| None | pSF128.1 | 30 | Gp140 | 30 |
| LPS antagonist (1 µg/ml) | pSF128.1 | 100 | Gp140 | 100 |
| LPS antagonist (3 µg/ml) | pSF128.1 | 300 | Gp140 | 1000 |
| LPS antagonist (10 µg/ml) | pSF128.1 | 30 | Gp140 | 100 |
| LPS antagonist (30 µg/ml) | pSF128.1 | 30 | Gp140 | 100 |
| MPLA (50 µg) | pSF128.1 | 300 | Gp140 | 1000 |

The results show that the LPS antagonist is a strong adjuvant for DNA vaccines and that it displays adjuvant properties similar to those displayed by MPLA when formulated with a DNA vaccine. Although all doses of the LPS antagonist elevated the level of the gp140-specific IgG response compared to the control DNA vaccine, surprisingly the peak priming effect occurred with 3 µg of LPS antagonist.

A similar adjuvant effect can be obtained in rabbits, guinea pigs and rats using the above outlined approach and injecting the preparations containing pSF128.2 and LPS antagonist subcutaneously, intramuscularly or intranasally.

6.5 Example 5

Increased Immunogenicity of a Polysaccharide Vaccine

This Example demonstrates the potent adjuvant activity of an LPS antagonist when administered together with a polysaccharide vaccine to an animal.

Vaccine preparations containing an LPS antagonist and a polysaccharide were prepared in the following manner. The antigen used in this Example consists of endotoxin-free *Salmonella typhi* Vi polysaccharide. Antibodies directed against this polysaccharide vaccine antigen have been shown to be protective in animals and humans. Vi polysaccharide has been used in field trials to provide protection against typhoid fever (Robbins and Robbins, 1984, supra; Klugman., et al., 1996, supra). Preparations comprised of Vi and LPS antagonist were formulated essentially as outlined in Example 2 above, except that each group received the following doses: 0.001, 0.01, 0.1 or 1 mg of Vi combined with a range of LPS antagonist doses (from 1–30 µg), using a conventional checkerboard approach as described above (see Table 6, groups 1.1–4.4). The LPS antagonist was isolated from MLK986 cultured at 37° C. as described above.

TABLE 6

Experimental design

| | 0.0001 mg Vi | 0.01 mg Vi | 0.1 mg Vi | 1.0 mg Vi |
|---|---|---|---|---|
| 1.0 µg LPS antagonist | Group 1.1 | Group 2.1 | Group 3.1 | Group 4.1 |
| 3.0 µg LPS antagonist | Group 1.2 | Group 2.2 | Group 3.2 | Group 4.2 |
| 10.0 µg LPS antagonist | Group 1.3 | Group 2.3 | Group 3.3 | Group 4.3 |
| 30.0 µg LPS antagonist | Group 1.4 | Group 2.4 | Group 3.4 | Group 4.4 |
| 0 µg LPS antagonist | Group 1.5 | Group 2.5 | Group 3.5 | Group 4.5 |
| 10.0 µg MPLA | Group 1.6 | Group 2.6 | Group 3.6 | Group 4.6 |

Groups of 3 BALB/c mice were injected subcutaneously with 0.1 ml of one of the above formulations, comprised of a given dose of Vi and LPS antagonist. To determine the immunogenicity of Vi in the absence of LPS antagonist, groups of 3 BALB/c mice were vaccinated with Vi formulated alone (see Table 5, groups 1.5–4.5). For comparative purposes, groups of mice were vaccinated with analogous doses of Vi polysaccharide formulated with 10 μg of MPLA (Ribi Co.) (see Table 5, groups 1.6–4.6), as directed by the manufacturer.

To measure the immunogenicity of each formulation, sera were collected from the mice in each group before and on days 14 and 28 after vaccination, as described in Example 2 above. The level of anti-gp120 IgG in pooled serum samples was determined by ELISA as described in Example 2 above, except that Vi (10 μg/ml) was used in place of Hep-Tat in the first coating step. The results of the ELISA were obtained by reading the optical density of each well using a Molecular Dynamics ELISA plate reader and showed that the LPS antagonist displays adjuvant properties when formulated with a Vi polysaccharide vaccine.

6.6 Example 6

New Method for Defining Culture Conditions to Produce Non Pyrogenic LPS and Lipid A with Strong Chemokine Inducing Activity This example describes a method for identifying culture conditions for the growth of gram negative bacteria, such as *E. coli* strain MLK986, that resulted in the synthesis of non pyrogenic LPS and lipid A with strong agonist activity for the induction of chemokine secretion. To that end we devised a checkerboard approach to assess the affect of temperature and magnesium concentration on the biological activity of LPS/lipid A in strain NJILK986 (see Table 7).

TABLE 7

| Medium | Temperature | | |
|---|---|---|---|
| | 30° C. | 37° C. | 40° C. |
| Low Mg++ | Preparation L1 | Preparation L2 | Preparation L3 |
| High Mg++ | Preparation H1 | Preparation H2 | Preparation H3 |

The low magnesium medium contained 50 mM Tris-HCi pH 7.4, 5 mM KCl, 7.5 mM $(NH_4)2SO_4$, 0.5 mM $K_2SO_4$, 1 mM $KH2PO_4$, 0.1% (w/v) casamino acids (Difco, Detroit Mich.) and 40 mM Glycerol. The high magnesium medium was Luria Bertani broth (LB broth) (Miller ed., in: A short course in Bacterial Genetics, Cold Spring Harbor Press, NY (1992D)) containing TTAB (8 μg/ml). Strain MLK 986 was cultured in each of the media at 30° C., 37° C. or 40° C. and LPS was extracted and purified by the hot-water phenol extraction procedure and assessed for purity as described in an earlier example above.

Figure 3:
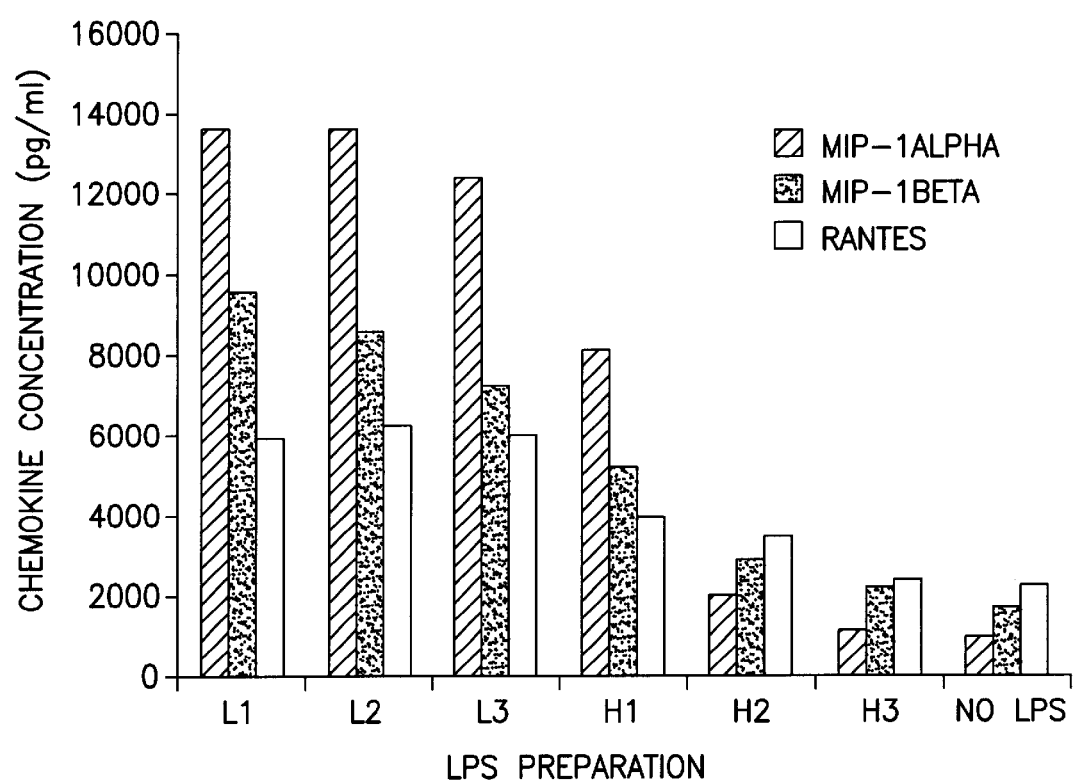
FIG. 3 is a graph of chemokine concentration of MIP-1α, MIP-1β and RANTES, for PBMC activation assays using LPS/lipid A in strain MLK986.

To assess the agonist activity of each preparation for the induction of β-chemokine secretion by human PBMCs we conducted a PBMC activation assay. Briefly, human PBMCs were obtained from whole blood as described (Crowley, et al. 1996, J. lmmunol, 156:2004). The PBMCs ($5×10_5$) were suspended in complete medium (CM; RPMI (Lifetechnologies, Bethesda Md.) containing 10 μg/ml of pyruvate and glutamine, 100 μg/ml of penicillin and streptomycin, and 10% (v/v) endotoxin-free human AB serum (Life Technologies)) and placed into 48 well flat-bottom culture plates (Costar). CM containing the LPS preparations was then added to these wells at a concentration of 100 ng/ml and the PBMCs were incubated at 37° C. in 5% $CO_2$. Culture supernatants were collected 24 hr after addition of the LPS preparations and MIP-1 a, MIP-1 β and RANTES levels in the culture supernatants were quantitated by capture ELISAs (R&D Systems). The results of this assay, shown in FIG. 3, demonstrate that the culture conditions substantially influence the magnitude of the agonist activity of the LPS produced by strain NILK986 for the induction of β-chemokine secretion by human PBMCs. In this experiment the β-chemokine-inducing agonist activity of the LPS isolated from MLK986 was strongest when this strain was cultured in low magnesium medium, at pH 7.4, and at 30° C. and 37° C. In a subsequent experiment the β-chemokine-inducing agonist activity of MLK986 LPS was significantly diminished in media buffered at pH 6.0. Hence, pH is an additional culture medium parameter that is useful for the purpose of identifying the specific culture conditions that generates non-pyrogenic LPS or lipid A with strong chemokine agonist activity. In such instances, the pH of the media could be varied from 4.0 to 9.0 depending on the particular strain being assessed.

In conclusion, therefore, we have devised a method for defining a culture condition that results in the synthesis of non-pyrogenic LPS or lipid A with strong chemokine inducing activity by a bacterial strain the harbors htrB and msbB mutations. Furthermore, in light of the conservation of the core lipid A, e.g., diphosphoryl-lipid A of *E. coli*, biosynthesis pathway in gram negative bacteria, this approach is fully adaptable and can be utilized to identify the specific culture conditions that generate non-pyrogenic LPS or lipid A with strong chemokine inducing activities using any gram negative strain. However, given that specific modifications to the core lipid A molecule varies among gram negative bacteria (e.g., the level of phosphate and ethanolamine substitution and the presence or absence of N-aminoarabinose and ether-linked palmitoyl substitutions), the preferred culture conditions of each strain may nevertheless vary somewhat. In any event, application of the method described above can be utilized to identify such preferred condition.

All of the above-cited references and publications are incorporated herein by reference. The disclosures of U.S. Provisional Patent Application Nos. 60/157,635 and 60/192, 650 are incorporated herein by reference in their entireties.

Equivalents

Those skilled in the art will recognize, or be able to ascertain using no more than routine experimentation, many equivalents to the specific embodiments of the invention described herein without departing from the spirit and scope thereof. Such equivalents are intended to be encompassed by the following claims.

What is claimed is:

1. A vaccine preparation comprising
   (i) a pharmaceutically effective amount of a substantially pure LPS antagonist isolated from a gram negative bacterium that is defective in at least one of the msbB or htrB genes, or an analog or derivative thereof, wherein the LPS antagonist has reduced pyrogenicity relative to an LPS antagonist isolated from the wildtype bacterium,
   (ii) a vaccine antigen, which is not isolated from the gram negative bacterium, and
   (iii) a pharmaceutically acceptable carrier.

2. The vaccine preparation of claim 1, wherein the LPS antagonist comprises an LPS molecule.

3. The vaccine preparation of claim 1, wherein the LPS antagonist comprises a lipid A molecule.

4. The vaccine preparation of claim 1, wherein the LPS antagonist consists of a heterologous mixture of LPS molecules, lipid A molecules, or LPS and lipid A molecules.

5. The vaccine preparation of claim 1, wherein the LPS antagonist inhibits an activity of a wildtype LPS by a factor of at least $10^2$.

6. The vaccine preparation of claim 5, wherein the LPS antagonist inhibits an activity of a wildtype LPS by a factor of at least $10^3$.

7. The vaccine preparation of claim 1, wherein the LPS antagonist has a pyrogenicity that is $10^5$ times lower than that of a wildtype LPS.

8. The vaccine preparation of claim 1, wherein the LPS antagonist increases an immune response to the antigen in a host at least $10^3$ fold relative to an immune response to the antigen administered to the host in the absence of the antagonist.

9. A vaccine preparation comprising a vaccine antigen and a pharmaceutically effective amount of a substantially pure preparation of an LPS antagonist.

10. The vaccine preparation of claim 1, wherein said vaccine antigen is a polysaccharide.

11. The vaccine preparation of claim 1, wherein said vaccine antigen is a peptide or protein.

12. The vaccine preparation of claim 1, wherein said vaccine antigen is a nucleic acid.

13. The vaccine preparation of claim 1, wherein the vaccine antigen elicits an immune reaction against a viral antigen.

14. The vaccine preparation of claim 13, wherein the vaccine antigen elicits an immune reaction against an antigen of a virus selected from the group consisting of orthomyxoviruses, retroviruses, herpesviruses, lentiviruses, rhabdoviruses, picornoviruses, poxviruses, rotavirus and parvoviruses.

15. The vaccine preparation of claim 14, wherein the vaccine antigen elicits an immune reaction against an antigen of a virus selected from the group consisting of influenza virus, RSV, EBV, CMV, herpes simplex virus, human immunodeficiency virus, rabies, poliovirus and vaccinia.

16. The vaccine preparation of claim 14, wherein the vaccine antigen elicits an immune reaction against an antigen selected from a group consisting of human immunodeficiency virus antigens Nef, p24, gp120, gp41, Tat, Rev, and Pol; T cell and B cell epitopes of gp120; the hepatitis B surface antigen; rotavirus antigens VP4 and VP7; influenza virus antigens hemagglutinin or nucleoprotein; and herpes simplex virus thymidine kinase.

17. The vaccine preparation of claim 1, wherein the vaccine antigen elicits an immune reaction against a bacterial pathogen.

18. The vaccine preparation of claim 17, wherein the bacterial pathogen is selected from the group consisting of Mycobacterium spp., *Helicobacter pylori*, Salmonella spp., Shigella spp., *E. coli*, Rickettsia spp., Listeria spp., *Legionella pneumoniae*, Pseudomonas spp., Vibrio spp., and *Borellia burgdorferi*.

19. The vaccine preparation of claim 17, wherein the vaccine antigen is derived from an antigen selected from the group consisting of the capsular polysaccharide of *Neisseria meningitis*; the Vi polysaccharide of *Salmonella enterica* serovar *typhi*; *Shigella sonnei* form 1 antigen; the O-antigen of *V. cholerae* Inaba strain 569; cholera toxin of *V. cholerae*; TCP of *V. cholera*; CFA/I fimbrial antigen of enterotoxigenic *E coli*; the heat-labile toxin of *E. coli*; pertactin of *Bordetella pertussis*;adenylate cyclase-hemolysin of *B. pertussis*; and fragment C of tetanus toxin of *Clostridium tetani*.

20. The vaccine preparation of claim 1, wherein the vaccine antigen is derived from a parasitic pathogen selected from the group consisting of Plasmodium spp., Trypanosome spp., Giardia spp., Boophilus spp., Babesia spp., Entamoeba spp., Eimeria spp., Leishmania spp., Schistosome spp. Brugia spp., Fascida spp., Dirofilaria spp., Wuchereria spp., and Onchocerea spp.

21. The vaccine preparation of claim 1, wherein the vaccine antigen is derived from an antigen selected from the group consisting of the circumsporozoite antigen of *P. berghei*, the circumsporozoite antigen of *P. falciparum*; the merozoite surface antigen of Plasmodium spp.; the galactose specific lectin of *Entamoeba histolytica*; gp63 of Leishmania spp.; paramyosin of *Brugia malayi*; the triose-phosphate isomerase of *Schistosoma mansoni*; the secreted globin-like protein of *Trichostrongylus colubriformis*; the glutathione-S-transferase of *Frasciola hepatica, Schistosoma bovis* and *S. japonicum*; and KLH of *Schistosoma bovis* and S.

22. The vaccine preparation of claim 1, wherein the vaccine antigen elicits an immune reaction against a tumor antigen.

23. The vaccine preparation of claim 22, wherein the tumor antigen is selected from the group consisting of prostate specific antigen, TAG-72, carcinoembrionic antigen (CEA), MAGE 1, tyrosinase, and mutant p53 antigen.

24. The vaccine preparation of claim 1, wherein the vaccine antigen elicits an immune reaction against the CD3 receptor on T cells.

25. The vaccine preparation of claim 1, wherein the vaccine antigen elicits an immune reaction against an autoimmune antigen.

26. The vaccine preparation of claim 1, wherein the autoimmune antigen is an IAS β chain.

27. The vaccine preparation of claim 1, wherein the vaccine antigen elicits an immune reaction aginst an immuno-stimulatory molecule selected from the group consisting of M-CSF, GM-CSF, IL-2, IL-4, IL-5, IL-6, IL-10, IL-12 and IFN-γ.

28. A method for preparing a vaccine preparation of claim 1, comprising combining a substantially pure LPS antagonist isolated from a gram negative bacterium that is defective in at least one of the msbB or htrB genes, or an analog or derivative thereof, wherein the LPS antagonist has reduced pyrogenicity relative to an LPS antagonist isolated from the wildtype bacterium; a vaccine antigen that is not derived from the bacterium; and a pharmaceutically acceptable carrier.

29. A method for inducing an immune response against an antigen in a subject, comprising administering to the subject a pharmaceutically effective amount of an LPS antagonist isolated from a gram negative bacterium that is defective in at least one of the msbB or htrB genes, or an analog or derivative thereof, wherein the LPS antagonist has reduced pyrogenicity relative to an LPS antagonist isolated from the wildtype bacterium and a vaccine antigen that is not derived from the bacterium, to thereby induce an immune response against the vaccine antigen in the subject.

30. The method of claim 29, wherein the LPS antagonist comprises an LPS molecule.

31. The method of claim 29, wherein the LPS antagonist comprises a lipid A molecule.

32. The method of claim 29, wherein the LPS antagonist consists of a heterologous mixture of LPS molecules, lipid A molecules, or LPS and lipid A molecules.

33. The method of claim 29, wherein the LPS antagonist inhibits an activity of a wildtype LPS by a factor of at least $10^2$.

34. The method of claim 29, wherein the LPS antagonist has a pyrogenicity that is $10^5$ times lower than that of a wildtype LPS.

35. The method of claim 29, wherein the LPS antagonist increases an immune response to the antigen in a host at least $10^3$ fold relative to an immune response to the antigen administered to the host in the absence of the antagonist.

36. A method for inducing an immune response against an antigen in a subject, comprising administering to the subject a vaccine antigen and a pharmaceutically effective amount of a substantially pure preparation of an LPS antagonist.

37. The method of claim 29, wherein said vaccine antigen is a polysaccharide.

38. The method of claim 29, wherein said vaccine antigen is a peptide or protein.

39. The method of claim 29, wherein said vaccine antigen is a nucleic acid.

40. The method of claim 29, wherein the vaccine antigen elicits an immune reaction against a viral antigen.

41. The method of claim 28, wherein the vaccine antigen elicits an immune reaction against an antigen of a virus selected from the group consisting of orthomyxoviruses, retroviruses, herpesviruses, lentiviruses, rhabdoviruses, picornoviruses, poxviruses, rotavirus and parvoviruses.

42. The method of claim 28, wherein the vaccine antigen elicits an immune reaction against an antigen of a virus selected from the group consisting of influenza virus, RSV, EBV, CMV, herpes simplex virus, human immunodeficiency virus, rabies, poliovirus and vaccinia.

43. The method of claim 29, wherein the vaccine antigen elicits an immune reaction against an antigen selected from a group consisting of human immunodeficiency virus antigens Nef, p24, gp 120, gp41, Tat, Rev, and Pol; T cell and B cell epitopes of gp120; the hepatitis B surface antigen; rotavirus antigen; VP4 and VP7; influenza virus antigens hemagglutinin or nucleoprotein; and herpes simplex virus thymidine kinase.

44. The method of claim 29, wherein the vaccine antigen elicits an immune reaction against a bacterial pathogen.

45. The method of claim 44, wherein the bacterial pathogen is selected from the group consisting of Mycobacterium spp., *Helicobacter pylori*, Salmonella spp., Shigella spp., *E. coli*, Rickettsia spp., Listeria spp., *Legionella pneumoniae*, Pseudomonas spp., Yibrio spp., and *Borellia burgdorferi*.

46. The method of claim 44, wherein the vaccine antigen is derived from an antigen selected from the group consisting of the capsular polysaccharide of *Neisseria meningitis*; the Vi polysaccharide of *Salmonella enterica* serovar *typhi*; *Shigella sonnei* form 1 antigen; the O-antigen of *V. cholerae* Inaba strain 569; cholera toxin of *V. cholerae*; TCP of *V. cholera*, CFA/I fimbrial antigen of enterotoxigenic *E coli*; the heat-labile toxin of *E coli*; pertactin of *Bordetella pertussis*;adenylate cyclase-hemolysin of *B. pertussis*; and fragment C of tetanus toxin of *Clostridium tetani*.

47. The method of claim 29, wherein the vaccine antigen is derived from a parasitic pathogen selected from the group consisting of Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp.

48. The method of claim 29, wherein the vaccine antigen is derived from an antigen selected from the group consisting of the circumsporozoite antigen of *P. berghei*, the circumsporozoite antigen of *P. falciparum*; the merozoite surface antigen of Plasmodium spp.; the galactose specific lectin of *Entamoeba histolytica*; gp63 of Leishmania spp.; paramyosin of *Brugia malayi*; the triose-phosphate isomerase of *Schistosoma mansoni*; the secreted globin-like protein of *Trichostrongylus colubriformis*; the glutathione-S-transferase of *Frasciola hepatica, Schistosoma bovis* and *S. japonicum*; and KLH of *Schistosoma bovis* and S.

49. The method of claim 29, wherein the vaccine antigen elicits an immune reaction against a tumor antigen.

50. The method of claim 29, wherein the tumor antigen is selected from the group consisting of prostate specific antigen, TAG-72, carcinoembrionic antigen (CEA), MADE-1, tyrosinase, and mutant p53 antigen.

51. The method of claim 29, wherein the vaccine antigen elicits an immune reaction against the CD3 receptor on T cells.

52. The method of claim 29, wherein the vaccine antigen elicits an immune reaction against an autoimmune antigen.

53. The method of claim 29, wherein the autoimmune antigen is an IAS β chain.

54. The method of claim 29, wherein the vaccine antigen elicits an immune reaction against an immuno-stimulatory molecule selected from the group consisting of M-CSF, GM-CSF, IL-2, IL-4, IL-5, IL-6, IL-10, IL-12 and IFN-γ.

55. A kit for inducing an immune reaction against an antigen in a subject, comprising a
  (i) pharmaceutically effective amount of a substantially pure LPS antagonist isolated from a gram negative bacterium that is defective in at least one of the msbB or htrB genes, or an analog or derivative thereof, wherein the LPS antagonist has reduced pyrogenicity relative to an LPS antagonist isolated from the wildtype bacterium, and
  (ii) a vaccine antigen, which is not isolated from the gram negative bacterium.

* * * * *

UNITED STATES PATENT AND TRADEMARK OFFICE
CERTIFICATE OF CORRECTION

PATENT NO. : 6,759,241 B1
DATED : July 6, 2004
INVENTOR(S) : Hone et al.

It is certified that error appears in the above-identified patent and that said Letters Patent is hereby corrected as shown below:

Column 5,
Line 1, "hirB" should be -- htrB --

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,759,241 B1 | Page 1 of 1 |
| APPLICATION NO. | : 10/110072 | |
| DATED | : July 6, 2004 | |
| INVENTOR(S) | : David Hone | |

It is certified that error appears in the above-identified patent and that said Letters Patent is hereby corrected as shown below:

Column 1, line 13, please add:

--GOVERNMENT SUPPORT
This invention was made with government support under Grant Nos. AI041914, AI042603 and AI043756 awarded by the National Institutes of Health, National Institute of Allergy and Infectious Diseases. The Government has certain rights in the invention.--

Signed and Sealed this
Fourth Day of January, 2011

David J. Kappos
*Director of the United States Patent and Trademark Office*